(12) United States Patent
Larter et al.

(10) Patent No.: US 9,068,107 B2
(45) Date of Patent: Jun. 30, 2015

(54) PROCESS FOR STIMULATING PRODUCTION OF METHANE FROM PETROLEUM IN SUBTERRANEAN FORMATIONS

(75) Inventors: Stephen Richard Larter, Calgary (CA); Ian McCutcheon Head, Ovingham (GB); David Martin Jones, Newcastle Upon Tyne (GB); Michael Erdmann, Nesttun (NO); Arnd Wilhelms, Fana (NO)

(73) Assignees: The University of Newcastle Upon Tyne, Newcastle Upon Tyne (GB); Norsk Hydro ASA, Oslo (NO)

(*) Notice: Subject to any disclaimer, the term of this patent is extended or adjusted under 35 U.S.C. 154(b) by 2080 days.

(21) Appl. No.: 11/569,706

(22) PCT Filed: May 27, 2005

(86) PCT No.: PCT/GB2005/002121
§ 371 (c)(1),
(2), (4) Date: Apr. 30, 2007

(87) PCT Pub. No.: WO2005/115649
PCT Pub. Date: Dec. 8, 2005

(65) Prior Publication Data
US 2007/0251146 A1 Nov. 1, 2007

(30) Foreign Application Priority Data
May 28, 2004 (GB) .................................. 0412060.6

(51) Int. Cl.
C12P 5/02 (2006.01)
C09K 8/582 (2006.01)

(52) U.S. Cl.
CPC .................. *C09K 8/582* (2013.01); *C12P 5/023* (2013.01); *Y02E 50/343* (2013.01)

(58) Field of Classification Search
CPC ............. B09C 1/10; C12P 3/00; C12P 5/023; C09K 8/582
USPC .............. 435/262, 281, 166, 262.5, 167, 168; 166/246; 507/201
See application file for complete search history.

(56) References Cited

U.S. PATENT DOCUMENTS

| | | | |
|---|---|---|---|
| 5,340,376 A | 8/1994 | Cunningham et al. | |
| 5,350,684 A | 9/1994 | Nakatsugawa et al. | |
| 5,464,539 A | 11/1995 | Ueno et al. | |
| 5,750,392 A | 5/1998 | Hitzman et al. | |
| 6,543,535 B2 | 4/2003 | Converse et al. | |
| 8,092,559 B2 | 1/2012 | Debruyn et al. | |
| 2004/0033557 A1 | 2/2004 | Scott et al. | |
| 2004/0050778 A1 | 3/2004 | Noike et al. | |
| 2007/0298479 A1 | 12/2007 | Larter et al. | |

FOREIGN PATENT DOCUMENTS

| | | |
|---|---|---|
| WO | WO 79/00201 | 4/1979 |
| WO | WO 01/68904 | 9/2001 |
| WO | WO 02/06503 | 1/2002 |
| WO | WO 2005/115648 | 12/2005 |
| WO | WO 2005/115649 | 12/2005 |
| WO | 2006/118569 | 11/2006 |

OTHER PUBLICATIONS

Kotelnikova."Microbial production and oxidation of methane in deep subsurface." Earch-Science Reviews, vol. 58 (2002), pp. 367-395.*
Schnell et al."Mechanistic Analysis of Ammonium Inhibition of Atmospheric Methane Consumption in Forest Soils". Applied and Environmental Microbiology, vol. 60, No. 10 (Oct. 1994), pp. 3514-3521.*
Aeckersberg, F. et al., "Anaerobic oxidation of saturated hydrocarbons to CO2 by a new type of sulfate-reducing bacterium," Arch Microbiol. (1991) 156:5-14.
Aitken, C.M. et al., "The detection and occurrence of anaerobic hydrocarbon metabolites in petroleum reservoirs," Abstraccts of the 2002 William Smith Meeting, Geological Society of London (Oct. 2002).

(Continued)

*Primary Examiner* — William H Beisner
(74) *Attorney, Agent, or Firm* — Foley & Lardner LLP

(57) ABSTRACT

A process for stimulating microbial methane production in a petroleum-bearing subterranean formation, comprising: (a) analyzing one or more components of the formation to determine characteristics of the formation environment; (b) detecting the presence of a microbial consortium, comprising at least one methanogenic microorganism, within the formation; (c) assessing whether the formation microorganisms are currently active; (d) determining whether the microbial consortium comprises one or more methanotrophic microorganism; (e) characterization of one or more microorganisms of the consortium, at least one of the members of the consortium being a methanogenic microorganism, and comparing the members of the consortium with at least one known microorganism having one or more known physiological and ecological characteristics; (f) characterization of one or more methanotrophic microorganisms of the consortium (if present), and comparing the members of the consortium with at least one known microorganism having one or more known physiological and ecological characteristics; (g) using information obtained from steps (a) through (e) for determining an ecological environment that promotes in situ microbial degradation of petroleum and promotes microbial generation of methane by at least one methanogenic microorganism of the consortium; (h) using information obtained from steps (a) and (f), if methanotrophic microorganisms are present, for determining an ecological environment that demotes in situ microbial degradation of methane by at least one methanotrophic microorganism of the consortium; and (i) modifying the formation environment based on the determinations of steps (g) and (h), if methanotrophic microorganisms are present, to stimulate microbial conversion of petroleums to methane while minimising methane destruction by adverse processes.

15 Claims, 3 Drawing Sheets

(56) References Cited

OTHER PUBLICATIONS

Aitken, C.M. et al., "Anaerobic hydrocarbon biodegradation in deep subsurface oil reservoirs," Nature (2004) 431:291-294.
Anderson, R.T. et al., "Hexadecane decay by methanogenesis," Nature (2000) 404:722-723.
Annweiler, E. et al., "Identical ring cleavage products during anaerobic degradation of nephthalene, 2-methylnaphthalene, and tetralin indicate a new metabolic pathway," App. Env. Microbiol. (2002) 68(2):852-858.
Belay, N. et al., "Dinitrogen fixation by a thermophilic methanogenic bacterium," Nature (1984) 312:286-288.
Beller, H.R., "Analysis of benzylsuccinates in groundwater by liquid chromatography/tandem mass spectrometry and its use for monitoring in situ BTEX biodegradation," Environ. Sci. Technol. (2002) 36:2724-2728.
Bernard, F.P. et al., "Indigenous microorganisms in connate water of many oil fields: a new tool in exploration and production techniques," 1992 SPE Annual Technical Conference and Exhibition (Oct. 4-7, 1992) Washington D.C., SPE24811:467-476.
Bennett, P.C. et al., "Microbial control of mineral-groundwater equilibria: macroscale to microscale," Hydrogeology Journal (2000) 8:47-62.
Bennett, P.C. et al., "Silicates, silicate weathering and microbial ecology," Geomicrobiology Journal (2001) 18:3-19.
Bennett, P.C. et al., "Crude oil in a shallow sand and gravel aquifer—I. Hydrogeology and inorganic geochemistry," Applied Geochemistry (1993) 8:529-549.
Bennett, P.C. et al., "Microbial colonization and weathering of silicates in a petroleum-contaminated groundwater," Chemical Geology (1996) 132:45-53.
Boone, D.R. et al., "Diversity and taxonomy of methanogens," Chapter 1 in *Methanogenesis Ecology, Physiology, Biochemistry & Genetics*, James G. Ferry, editor, Chapman & Hall, New York (1993) 35-80.
Boreham, C.J. et al., "Understanding source, distribution and preservation of Australian natural gas: a geochemical perspective," Appea Journal (2001) 523-547.
Borzenkov, I.A. et al., "Methanogenesis in the highly mineralized stratal waters of the Bondyuzhskoe oil field," Microbiology (1997) 66:104-110 Abstract.
Burggraf, S. et al., "*Methanopyrus kandleri*: an archaeal methanogen unrelated to all other known methanogens," System. Appl. Microbiol. (1991) 14:346-351.
Capone, D.G. et al., "Comparison of microbial dynamics in marine and freshwater sediments: Contrasts in anaerobic carbon catabolism," Limnol. Oceanogr. (1988) 33(4, part 2):725-749.
Chaston, S. et al., "The next iteration factor (NIF) method for calculating equilibrium conditions in subsurface waters, for the isolation of microorganisms from petroleum reservoirs," Aust. J. Chem. (1996) 49:943-949.
Coates, J.D. et al., "Diversity and ubiquity of bacteria capable of utilizing humic substances as electron donors for anaerobic respiration," App. Environ. Microbiol. (2002) 68(5):2445-2452.
Colwell, F.S. et al., "Innovative techniques for collection of saturated and unsaturated subsurface basalts and sediments for microbiological characterization," J. Microbiol. Meth. (1992) 15:279-292.
Connan, J., "Biodegradation of crude oils in reservoirs," Advances in Petroleum Geochemistry (1984) 1:299-335.
Dessort, D. et al., "Stable isotope geochemistry of gas associated to oil biodegradation," Abstracts of the 21st IMOG, Krakow, Poland (2003) 2 pages.
Ehrenreich, P. et al., "Anaerobic oxidation of alkanes by newly isolated denitrifying bacteria," Arch. Microbiol. (2000) 173:58-64.
Ehrenberg, S.N. et al., "Plagioclase dissolution related to biodegradation of oil in Brent Group sandstones (Middle Jurassic) of Gullfaks Field, northern North Sea," Sedimentology (2001) 48:703-721.
Fardeau, M.-L. et al., "Effect of thiosulphate as electron acceptor on glucose and xylose oxidation by *Thermoanaerobacter finnii* and a *Thermoanaerobacter* sp. isolated from oil field water," Res. Microbiol. (1996) 147:159-165.

Ficker, M. et al., "Molecular characterization of a toluene-degrading methanogenic consortium," App. Environ. Microbiol. (1999) 65(12):5576-5585.
Fries, M.R. et al., "Isolation, characterization, and distribution of denitrifying toluene degraders from a variety of habitats," App. Environ. Microbiol. (1994) 60(8):2802-2810.
Galushko, A. et al., "Anaerobic degradation of naphthalene by a pure culture of a novel type of marine sulphate-reducing bacterium," Environ. Microbiol. (1999) 1(5):415-420.
Garcia, J-L. et al., "Taxonomic, phylogenetic, and ecological diversity of methanogenic archaea," Anaerobe (2000) 6:205-226.
Grassia, G.S. et al., "A systematic survey for thermophilic fermentative bacteria and archaea in high temperature petroleum reservoirs," FEMS Microbiol. Ecol. (1996) 21:47-58.
Grbic-Galic, D. et al., "Transformation of toluene and benzene by mixed methanogenic cultures," App. Environ. Microbiol. (1987) 53(2):254-260.
Gray, N.D. et al., "Linking genetic identity and function in communities of uncultured bacteria," Environ. Microbiol. (2001) 3(8):481-492.
Hallam, S.J. et al., "Identification of methyl coenzyme M reductase A (mcrA) genes associated with methane-oxidizing archaea," App. Environ. Microbiol. (2003) 69(9):5483-5491.
Head, I.M. et al., "Microbial evolution, diversity, and ecology: a decade of ribosomal RNA analysis of uncultivated microorganisms," Microb. Ecol. (1998) 35:1-21.
Head, I.M., "Recovery and analysis of ribosomal RNA sequences from the environment," Chapter 11 in Methods in Biotechnology, vol. 12 Environmental Monitoring of Bacteria, Clive Edwards, editor, Humana Press, New Jersey (1999) 139-174.
Head, I.M. et al., "Biological activity in the deep subsurface and the origin of heavy oil," Nature (2003) 426:344-352.
Heritier, F.E. et al., "Frigg Field—large submarine-fan trap in lower eocene rocks of North Sea Viking Graben," Amer. Assoc. Petro. Geologists Bulletin (1979) 63(11):1999-2020.
Hernandez, M.E. et al., "Extracellular electron transfer," Cell. Mol. Life. Sci. (2001) 58:1562-1571.
Hiebert, F.K. et al., "Microbial control of silicate weathering in organic-rich ground water," Science (1992) 258:278-281.
Horstad, I. et al., "Degradation and maturity controls on oil field petroleum column heterogeneity in the Fullfaks field, Norwegian North Sea," Org. Geochem. (1990) 16(1-3):497-510.
Horstad, I. et al., "Petroleum migration, atleration, and remigration within Troll Field, Norwegian North Sea," AAPG Bulletin (1997) 81(2):222-248.
Hunkeler, D. et al., "Petroleum hydrocarbon mineralization in anaerobic laboratory aquifer columns," J. Contaminant Hydrology (1998) 32:41-61.
James, A.T. et al., "Microbial alteration of subsurface natural gas accumulations," Amer. Assoc. Petro. Geologists Bulletin (1984) 68(8):957-960.
Kamagata, Y. et al., "Isolation and characterization of a novel thermophilic methanosaeta strain," Int. J. Systematic Bacteriology (1991) 41(2):191-196.
Kostka, J.E. et al., "The impact of structural Fe(III) reduction by bacteria on the surface chemistry of smectite clay minerals," Geochimica et Cosmochimica Acta (1999) 63(22):3705-3713.
Kruger, M. et al., "A conspiculous nickel protein in microbial mats that oxidize methane anaerobically," Nature (2003) 426:878-881.
Lanoil, B.D. et al., "Bacteria and archaea physically associated with Gulf of Mexico gas hydrates," App. Environ. Microbiol. (2001) 67(11):5143-5153.
Larter, S. et al., "Natural gas formation and occurrence," Proceedings from the AAPG Hedberg Research Conference, Durango, Colorado (Jun. 6-11, 1999).
Larter, S. et al., "The controls on the composition of biodegraded oils in the deep subsurface—part 1: biodegradation rates in petroleum reservoirs," Org. Geochem. (2003) 34:601-613.
L'Haridon, S. et al., "Hot subterranean biosphere in a continental oil reservoir," Nature (1995) 377:223-224.
Lovley, D.R. et al., "Kinetic analysis of competition between sulfate reducers and methanogens for hydrogen in sediments," App. Environ. Microbiol. (1982) 43(6):1373-1379.

(56) References Cited

OTHER PUBLICATIONS

Lovley, D.R. et al., "Sulfate reducers can outcompete methanogens at freshwater sulfate concentrations," Appl. Environm. Microbiol. (1983) 45(1):187-192.

Lovley, D.R. et al., "Competitive mechanisms for inhibition of sulfate reduction and methane production in the zone of ferric iron reduction in sediments," Appl. Environ. Microbiol. (1987) 53(11):2636-2641.

Lovley, D.R. et al., "Hydrogen concentrations as an indicator of the predominant terminal electron-accepting reactions in aquatic sediments," Geochimica et Cosmochimica Acta (1988) 52:2993-3003.

Lovley, D.R. et al., "Oxidation of aromatic contaminants coupled to microbial iron reduction," Nature (1989) 339:297-300.

Lovley, D.R. et al., "Anaerobic benzene degradation," Biodegradation (2000) 11:107-116.

Lueders, T. et al., "Evaluation of PCR amplification bias by terminal restriction fragment length polymorphism analysis of small-subunit rRNA and mcrA genes by using defined template mixtures of methanogenic pure cultures and soil DNA extracts," Appl. Environ. Microbiol. (2003) 69(1):320-326.

Magot, M. et al., "Microbiology of petroleum reservoirs," Antonie van Leeuwenhoek (2000) 77:103-116.

Manning, D.A.C. et al., "Distribution and mineralogical controls on ammonium in deep groundwaters," Appl. Geochem. (2004) 19:1495-1503.

Marchesi, J.R. et al., "Methanogen and bacterial diversity and distribution in deep gas hydrate sediments from the Cascadia Margin as revealed by 16S rRNA molecular analysis," FEMS Microbiology Ecology (2001) 34:221-228.

Masterson, W.D. et al., "Evidence for biodegradation and evaporative fractionation in West Sak, Kuparuk and Prudhoe Bay field areas, North Slope, Alaska," Organic Geochem. (2001) 32:411-441.

Mountfort, D.O. et al., "Isolation and characterization of an anaerobic syntrophic benzoate-degrading bacterium from sewage sludge," Arch. Microbiol. (1982) 133:249-256.

Mueller, R.F. et al., "Characterization of thermophilic consortia from two souring oil reservoirs," Appl. Environ. Microbiol. (1996) 62(9):3083-3087.

Murray, P.A. et al., "Nitrogen fixation by a methanogenic archaebacterium," Nature (1984) 312:284-286.

Nazina, T.N. et al., "Occurrence and geochemical activity of microorganisms in high-temperature, water-flooded oil fields of Kazakhstan and Western Siberia," Geomicrobiol. J. (1995) 13:181-192.

Nazina, T.N. et al., "Occurrence of sulfate- and iron-reducing bacteria in stratal waters of the Romashkinskoe oil field," Microbiology (1995) 64(2):203-208.

Ng, T.K. et al., "Possible nonanthropogenic origin of two methanogenic isolates from oil-producing wells in the San Miguelito Field, Ventura County, California," Geomicrobiol. J. (1939) 7:185-192.

Nilsen, R.K. et al., "*Methanococcus thermolithotrophicus* isolated from North Sea Oil field reservoir water," Appl. Environ. Microbiol. (1996) 62(2):728-731.

Obraztsova, A.Y. et al., "Biological properties of methanosarcina not utilizing carbonic acid and hydrogen," Mikrobiologiya (1987) 56(6):1016-1021.

Obraztsova, A.Y. et al., "Properties of the coccoid methylotrophic methanogen," Mikrobiologiya (1987) 56(4):661-665.

Oremland, R.S. et al., "Use of 'specific' inhibitors in biogeochemistry and microbial ecology," Advances in Microbial Ecology (1988) 10:285-383.

Orphan, V.J. et al., "Culture-dependent and culture-independent characterization of microbial assemblages associated with high-temperature petroleum reservoirs," Appl. Environ. Microbiol. (2000) 66(2):700-711.

Pallasser, R.J., "Recognising biodegradation in gas/oil accumulations through the $\delta^{13}C$ compositions of gas components," Organic Geochem. (2000) 31:1363-1373.

Phelps, C.D. et al., "Metabolic biomarkers for monitoring anaerobic naphthalene biodegradation in situ," Environ. Microbiol. (2002) 4(9):532-537.

Phipps, B.M. et al., "A novel ATPase complex selectively accumulated upon heat shock is a major cellular component of thermophilic archaebacteria," EMBO Journal (1991) 10(7):1711-1722.

Rabus, R. et al., "Anaerobic initial reaction of n-alkanes in a denitrifying bacterium: evidence for (1-methylpentyl)succinate as initial product and for involvement of an organic radical in n-hexane metabolism," J. Bacteriol. (2001) 183(5):1707-1715.

Ravot, G. et al., "Thiosulfate reduction, an important physiological feature shared by members of the order thermotogales," Appl. Environ. Microbiol. (1995) 61(5):2053-2055.

Ravot, G. et al., "*Thermotoga elfii* sp. nov., a novel thermophilic bacterium from an African oil-producing well," Int. J. Systematic Bacteriol. (1995) 45(2):308-314.

Reeburgh, W.S., "Rates of biogeochemical processes in anoxic sediments," Ann. Rev. Earth Planet Sci. (1983) 11:269-298.

Richnow, H.H. et al., "Methane formation during the degradation of N-alkanes and total crude oils," J. Conf. Abstracts (2000) 5(2):844.

Roadifer, R.E., "Size distributions of the world's largest known oil and tar accumulations," AAPG Studies in Geology (2003) 25:3-23.

Rockne, K.J. et al., "Anaerobic naphthalene degradation by microbial pure cultures under nitrate-reducing conditions," Appl. Environ. Microbiol. (2000) 66(4):1595-1601.

Rogers, J.R. et al., "Mineral stimulation of subsurface microorganisms: release of limiting nutrients from silicates," Chem. Geol. (2004) 203:91-108.

Rogers, J.R. et al., "Feldspars as a source of nutrients for microorganisms," Amer. Mineralogist (1998) 83:1532-1540.

Roling, W.F. et al., "Prokaryotic systematics: PCR and sequence analysis of amplified 16S rRNA genes," Advanced Methods in Molecular Microbial Ecology (ed: Osborn and Smith, Taylor and Francis, Abingdon, UK) (2005) 25-63.

Roling, W.F.M. et al., "The microbiology of hydrocarbon degradation in subsurface petroleum reservoirs: perspectives and prospects," Research in Microbiology (2003) 154:321-328.

Rozanova, E.P. et al., "Microbial processes in the Savuiskoe oil field in the Ob Region," Microbiology (1995) 64(1):85-90.

Rueter, P. et al., "Anaerobic oxidation of hydrocarbons in crude oil by new types of sulphate-reducing bacteria," Nature (1994) 372:455-458.

Schink, B., "Energetics of syntrophic cooperation in methanogenic degradation," Microbiol Mol. Biol. (1997) 61(2):262-280.

Scott, A.R. et al., "Thermogenic and secondary biogenic gases, San Juan Basin, Colorado and New Mexico—Implications for coalbed gas producibility," AAPG Bulletin (1994) 78(8):1186-1209.

Sekiguchi, Y. et al., "*Syntrophothermus lipocalidus* gen. nov., sp. nov., a novel thermophilic, syntrophic, fatty-acid-oxidizing anaerobe which utilizes isobutyrate," Int. J. Systematic and Evolutionary Microbiology (2000) 50:771-779.

Slobodkin, A.I. et al., "Dissimilatory reduction of Fe(III) by thermophilic bacteria and archaea in deep subsurface petroleum reservoirs of Western Siberia," Current Microbiology (1999) 39:99-102.

So, C.M. et al., "Isolation and characterization of a sulfate-reducing bacterium that anaerobically degrades alkanes," Appl. Environ. Microbiol. (1999) 65(7):2969-2976.

Stahl, D.A., "Molecular approaches for the measurement of density, diversity and phylogeny," Chapter 11 in the Manual of Environmental Microbiology, Hurst et al. editors, ASM Press, Washington, DC (1997) 102-114.

Stettner, K.O. et al., "The role of hyperthermophilic prokaryotes in oil fields," Proceedings of the 8th International Symposium on Microbial Ecology (eds: Bell et al.) Halifax, Canada (2000) 369-375.

Stettner, K.O. et al., "Hyperthermophilic archaea are thriving in deep North Sea and Alaskan oil reservoirs," Nature (1993) 365:743-745.

Sweeney, R.E. et al., "Biogenic methane derived from the biodegradation of petroleum under environmental conditions and in oil and gas reservoirs," AAPG Hedberg Research Conference "Natural Gas Formation and Occurrence," (Jun. 6-10, 1999) Durango, Colorado, 2 pages.

(56) References Cited

OTHER PUBLICATIONS

Takahata, Y. et al., "Starvation survivability of *Thermococcus* strains isolated from Japanese oil reservoirs," Arch. Microbiol. (2001) 176:264-270.
Takahata, Y. et al., "Distribution and physiological characteristics of hyperthermophiles in the Kubiki Oil Reservoir in Niigata, Japan," Appl. Environ. Microbiol. (2000) 66(1):73-79.
Tardy-Jacquenod, C. et al., "Characterization of sulfate-reducing bacteria isolated from oil-field waters," Can. J. Microbiol. (1996) 42:259-266.
Thauer, R.K. et al., "Energy conservation in chemotrophic anaerobic bacteria," Bacteriological Reviews (1977) 41(1):100-180.
Truper, H.G. et al., "Prokaryote characterization and identification," Chapter 5 in The Prokaryotes, Second Edition, vol. 1, Balows et al. editors, Springer-Verlag, New York (1981) 126-148.
Vargas, M. et al., "Microbiological evidence for FE(III) reduction on early Earth," Nature (1998) 395:65-67.
Wallrabenstein, C. et al., "Pure culture of *Syntrophus buswellii*, definition of its phylogenetic status, and description of *Syntrophus gentianae* sp. nov.," System. Appl. Microbiol. (1995) 18:62-66.
Weiner, J.M. et al., "Rapid benzene degradation in methanogenic sediments from a petroleum-contaminated aquifer," Appl. Environ. Microbiol. (1998) 64(5):1937-1939.
Wellsbury, P. et al., "Deep marine biosphere fuelled by increasing organic matter availability during burial and heating," Nature (1997) 388:573-576.
Wenger, L.M. et al., "Multiple controls on petroleum biodegradation and impact on oil quality," Society of Petroleum Engineers (2001) SPE71450.
Whitman, W.B. et al., "The methanogenic bacteria," The Prokaryotes (eds: Balows et al.) Chapter 33 (1992) 719-767.
Widdel, F. et al., "Anaerobic biodegradation of saturated and aromatic hydrocarbons," Curr. Opin. Biotech. (2001) 12:259-276.
Wilhelms, A. et al., "Biodegradation of oil in uplifted basins prevented by deep-burial sterilization," Nature (2001) 411:1034-1037.
Wilkes, H. et al., "Anaerobic degradation of n-hexane in a denitrifying bacterium: further degradation of the initial intermediate (1-methylpentyl)succinate via C-skeleton rearrangement," Arch. Microbiol. (2002) 177:235-243.
Wilkes, H. et al., "Anaerobic degradation and carbon isotopic fractionation of alkylbenzenes in crude oil by sulphate-reducing bacteria," Org. Geochem. (2000) 31:101-115.
Zengler, K. et al., "Methane formation from long-chain alkanes by anaerobic microorganisms," Nature (1999) 401:266-269.
Zinder, S.H. et al., "*Methanosarcina thermophila* sp. nov., a thermophilic, acetotrophic, methane-producing bacterium," Int. J. Systematic Bacteriology (1985) 35(4):522-523.
International Search Report and Written Opinion for Application No. PCT/GB2005/002121 dated Sep. 6, 2005 (8 pages).
International Report on Patentability for Application No. PCT/GB2005/002121 dated Aug. 24, 2006 (8 pages).
International Search Report and Written Opinion for Application No. PCT/GB2005/002109 dated Sep. 2, 2005 (8 pages).
International Report on Patentability for Application No. PCT/GB2005/002109 dated Aug. 24, 2006 (7 pages).
Koga, Y. et al., "Ether polar lipids of methanogenic bacteria: structures, comparative aspects, and biosyntheses," Microbiol. Rev. (1993) 57(1):164-182.
United States Patent Office Action for U.S. Appl. No. 11/569,712 dated Oct. 4, 2010 (12 pages).
United States Patent Office Action for U.S. Appl. No. 11/569,712 dated Jun. 10, 2011 (13 pages).

\* cited by examiner

SEQUENCE LISTING

<160> NUMBER OF SEQ ID NOS: 7

<210> SEQ ID NO 1
<211> LENGTH: 868
<212> TYPE: DNA
<213> ORGANISM: Artificial
<220> FEATURE:
<223> OTHER INFORMATION: Synthetic Oligonucleotide (ATS10C)

<400> SEQUENCE: 1

```
gctcattaac atgtggacaa tctacccttg ggtagggggat aaccttggga aactgaggat      60
aaaaccctat aggcatagaa tgctggaatg cttctatgtt aaaaggcaac gcccaaggat     120
gagtctgcaa cctattaggc tgtagcaggt gtaatgcact tgttaaccta tgatgggtac     180
gggccatgaa agtggttgcc cggagatgga ctctgagaca tgagtccagg ccctacgggg     240
cgcagcaggc gcgaaaactt cgcaatgtgc gcaagcacga cggggggaatc ctaagtgcct    300
atgctttgca taggctgttc tcctgtctaa aaaatagggg aagtaaggc tgggtaagac      360
gggtgccagc cgccgcggta atacccgcag cccaagtggt gatcgttatt attgggtcta    420
aaacgtccgt agctggtttg gtaaattcct gggtaaatcg agctgcctaa cagttcgaat    480
tctgggaga ctgccagact tgggaccggg aggagtcaga agtactttcg gggtaggggt      540
aaaatcctgc aatcctgaaa ggactatcag cggcgaaggc gtctgaccag aacgatccg     600
acagtaaggg acgaagccct ggggcgcaaa cgggattaga taccccggta gtccaggtg     660
taaacgctgt aggcttggtg ctgggggttc tacgaggaca cacagtgccg gagagaagtt    720
gttaagccta ctacctgggg agtacggtcg caagactgaa acttaaagga attggcgggg    780
gagcaccgca acgggtggag cgtgcggttt aattggattc aacgccggaa aactcaccgg    840
gagcgacggt tacatgaagg ccaggcta                                        868
```

<210> SEQ ID NO 2
<211> LENGTH: 900
<212> TYPE: DNA
<213> ORGANISM: Artificial
<220> FEATURE:
<223> OTHER INFORMATION: Synthetic Oligonucleotide (ATS29A)

<400> SEQUENCE: 2

```
cacgtggaca atctaccctt cggtgggga taatcttggg aaactgagaa taataccccca     60
taggcctagg atgctggaat gcttctaagc tgaaagttcc gacgccgaag gatgagtctg    120
cggcctatca ggttgtagca agtgtaatgc acttgttagc ctacaacggg tacgggccat    180
gagagtggtt gcccggagat ggactctgag acatgagtcc aggccctacg ggcgcagca    240
ggcgcgaaaa cttcgcaatg tgcgcaagca cgacgaggga atcctaagtg cctatgcttt    300
gcataggctg ttctcctgtc taaaaaacag gggagtaag gctgggtaa gacgggtgcc      360
agccgccgcg gtaatacccg cagcccaagt ggtgatcgtt attattgggt ttaaaatgtc    420
cgtagctggt ctagtaaatt cctgggtaaa tcgaattgct taacaattcg aattccggt     480
agactgctag acttgggacc ggaagaagtc agaagtactt ctggggtagg ggtaaaatcc    540
tgtaatcctg gagggactat caatggcgaa atttcggaag caaatcttcc tcatttatcg    600
ttgcttccgc aacgctaagg cgtctgacta gaacggatcc gacagtaagg gacgaagccc    660
tggggcgcaa acgggattag ataccccggt agtccaggt gtaaacgctg taggcttggt    720
gttgggggtc ctatgaggac atccagtgcc ggagagaaat tgttaagcct actacctggg    780
gagtacggtc gcaggactga aacttaaagg aattggcggg ggagcaccgc aacgggtgga    840
```

```
gcgtgcggtt taattggatt caacgccgga aacctcaccg ggggcgacgg ttatatgaag    900
```

<210> SEQ ID NO 3
<211> LENGTH: 850
<212> TYPE: DNA
<213> ORGANISM: Artificial
<220> FEATURE:
<223> OTHER INFORMATION: Synthetic Oligonucleotide (ATS29C)

<400> SEQUENCE: 3

```
catgtggaca atctacccett gggtagggga taaccttggg aaactgagga taaaaccecta    60
taggcataga atgctggaat gcttctatgt taaaaggcaa cgcccaagga tgagtctgca   120
acctattagg ctgtagcaag tgtaatgcac ttgttaacct atgatgggta cgggccatga   180
aagtggttgc ccggaggtgg actctgagac atgagtccag ccctacggg cgcagcagg    240
cgcgaaaact tcgcaatgtg cgcaagcacg acgaggaat cctaagtgcc tatgctttgc    300
ataggctgtt ctcctgtcta aaaatagggg gaagtaaggg ctgggtaaga cgggtgccag    360
ccgccgcggt aatacccgca gcccaagtgg tgatcgttat tattgggtct aaaacgtccg    420
tagctggttt ggtaaattcc tgggtaaatc gagctgccta acagttcgaa ttctggggag    480
actgccagac ttgggaccgg gaggagtcag aagtactttc ggggtagggg taaaatcctg    540
taatcctgaa aggactatca gcggcgaagg cgtctgacca aacggatcc gacagtaagg     600
gacgaagccc tggggcgcaa acgggattag ataccccggt agtccagggt gtaaacgctg    660
taggcttggt gctgggggtt ctacgaggac acacagtgcc ggagagaagt tgttaagcct    720
actacctggg gagtacggtc gcaagactga aacctaaagg aattggcggg ggagcaccgc    780
aacgggtgga gcgtgcggtt taattggatt caacgccgga aaactcaccg ggagcgacgg    840
ttacatgaag                                                          850
```

<210> SEQ ID NO 4
<211> LENGTH: 490
<212> TYPE: DNA
<213> ORGANISM: Artificial
<220> FEATURE:
<223> OTHER INFORMATION: Synthetic Oligonucleotide (ATS13b)
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t

<400> SEQUENCE: 4

```
tctgagtgcc tcctaaggag gctgttcaga tgtttaaaaa gcatctggag gaagggctgg     60
gcaagaccgg tgccagccgc cgcggtaaca ccggcagccc aagtggtagt cctgcttact    120
gggtctaaag cgtccgtagc cggccgggta agttccttgg gaaatttgat cgcttaacga    180
tcaagctacc tgggaatact acttggcttg ggaccgggag aggtcagagg tacttcaagg    240
```

```
gtaggggtga aatccgttaa tccttggggg accaccagta gcgaaggcgt ctgatcagac    300
cggatccgac ggtgagggac naaggctagg ggagcgaagc ggattagata cccgcgtagt    360
cctggctgta aacgatgcgg gctaggtatt ggcattactg cnagtgatgc cagtgctgaa    420
nggaatccgt taagcccgcc atctggggaa tacggtcgca aggctgaaac ttaaaggaat    480 tgncggggga                                                          490
```

```
<210> SEQ ID NO 5
<211> LENGTH: 542
<212> TYPE: DNA
<213> ORGANISM: Artificial
<220> FEATURE:
<223> OTHER INFORMATION: Synthetic Oligonucleotide (ATS17a)
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t

<400> SEQUENCE: 5
```

```
cctaagtgcc tatgctttgc ataggctgtt ctcctgtcta aaaacaggg ggagtaaggg     60 ctgggtaaga cgggtgccag ccgccgcggt aatacccgca gcccaagtgg tgatcattat    120
tattgggttt aaaatgtccg tagctggtct agtaaattcc tgggtaaatc gaattgctta    180
acaattcgaa ttccgggtag actgctagac ttgggaccgg aagaggtcag aagtacttct    240
ggggtagggg taaaatcctg taatcctgga gggactatca gtggcgaaat tcggaagca    300 aatcttcctc atttatcgtt gcttccgcaa cgctaaggcg tctgactaga acggatccga    360
cagtaaggga cgaagccctg gggcgcaaac gggattagat accccggtag tccagggtgt    420
aaacgctgta agcttggtgt tggggtcct atgangacat ccaatgccgg agaaaaattg    480
ttaagcctac tacctgggga gtacngtccg caagactgaa acttaaagga attggcgggg    540
ga                                                                  542
```

```
<210> SEQ ID NO 6
<211> LENGTH: 493
<212> TYPE: DNA
<213> ORGANISM: Artificial
<220> FEATURE:
<223> OTHER INFORMATION: Synthetic Oligonucleotide (ATS21c)
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (407)..(407)
```

<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t

<400> SEQUENCE: 6

```
cttaatgcct atgcttttgc ataggctgtt ccctgtctaa aaaatangg gaagtaaggg     60 ctgggtaaga cgggtgccan ccgccgcggt aatacccgca gcccaagtgg tgatcgttat    120
tattgggtct aaaacgtccg tagctggtct ggtaaattcc tgggtaaatc gagctgccta    180
acagttcgaa ttctgaggag actgccagac ttgggaccgg gaggagtcag aagtactttc    240
ggggtagggg taaaatcctg taatcctgaa aggacgatca gcggcgaang cgtctgacca    300
gaacggatcc gacagtaagg gacgaagccc tggggcgcaa acgggattag ataccccggt    360
agtccagggt gtaaacgctg tangcttggt gctgggagtt ctacnangac acccantgcc    420
gganagaagt tgttaagcct actacctggg gagtacggtc gcaagactga aacttaaagg    480
aattggcggg gga                                                      493
```

<210> SEQ ID NO 7
<211> LENGTH: 490
<212> TYPE: DNA
<213> ORGANISM: Artificial
<220> FEATURE:
<223> OTHER INFORMATION: Synthetic Oligonucleotide (ATS23a)
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t

<400> SEQUENCE: 7

```
ctgaagtgcc tcctaaggag gctgttcaga tgtttaaaaa gcatctggag gaagggctgg     60
gcaagaccgg tgccagccgc cgcggtaaca ccggcagccc aagtggtagt catgcttact    120
gggtctaaag cgtccgtagc cggccgggta agttccttgg gaaatttgat cgcttaacga    180
tcaagctacc tgggaatact acttggcttg gaccgggag aggtcagagg tacttcaagg    240
gtaggggtga aatccgttaa tccttggggg accaccagta gcgaaggcgt ctgatcagac    300
cggatccgac ggtgagggac gaaggctang ggagcnaagc ggattagata cccgcgtagt    360
cctagctgta aacgatgcgg gctaggtatt ggcattactg cgagtgatgc cagtgccgaa    420
nggaagccgn taagcccgcc atctgggaa tacggtcgca angcttaaac ttaaaggaat    480
tggcggggga                                                          490
```

PROCESS FOR STIMULATING PRODUCTION OF METHANE FROM PETROLEUM IN SUBTERRANEAN FORMATIONS

CROSS-REFERENCE TO RELATED APPLICATIONS

This patent application is a national stage filing under 35 U.S.C. 371 of International Application No. PCT/GB2005/002121, filed on May 27, 2005, which claims foreign priority benefits to United Kingdom Application No. 0412060.6, filed May 28, 2004.

This invention relates to a process of converting petroleum and other fossil fuels to methane in a subterranean formation at an economically significant rate using microbial action and recovering the methane.

BACKGROUND

'Petroleum' means crude oil including heavy and residual oils in any reservoir, bitumen in tar sands, natural gas, gas condensate and any hydrocarbon containing fluid producible through boreholes or solid and fluid hydrocarbon containing materials recoverable from mining of tar sands or bitumen containing reservoirs of any type.

When oil is present in porous and permeable subterranean rock formations such as sandstone, carbonate, chert, shale or fractured rocks of any type, it can generally be exploited by drilling into the oil-bearing formation and allowing existing pressure gradients to force the oil through the reservoir and up into a borehole. This process is known as primary recovery.

If and when the pressure gradients are insufficient to produce oil at the desired rate, it is common to carry out an improved recovery method to recover additional oil. This process is known as secondary recovery.

There are several secondary recovery techniques, including gas injection and water injection. Choice of a specific secondary recovery technique depends on the specifics of the petroleum accumulation. Water injection or water flooding is the most common secondary recovery technique. In water flooding, pressurized water is injected into the petroleum-bearing formation and oil and/or gas is produced from neighbouring petroleum production wells. First petroleum, and subsequently petroleum and water are recovered from the production well.

However, even after secondary recovery, a significant portion of petroleum remains in the formation, usually in excess of 50% and in some cases over 75% of the original petroleum in place. The fraction of unrecoverable petroleum is typically highest for heavy oils, bitumens, and petroleum in complex reservoir formations. In many oil fields, a very large fraction of the oil (40% or much more) can be left after conventional waterflooding. Much of this remaining oil is trapped due to capillary forces or adsorption onto mineral surfaces and represents an irreducible oil saturation. Additional oil is trapped as bypassed oil within the reservoir rock formation missed by primary and secondary recovery techniques. This remaining residual oil may be recovered by enhanced recovery techniques. One enhanced oil recovery technique uses microorganisms (either indigenous or introduced artificially) to displace the trapped or adsorbed oil from the rock. The goal of this technique, which is known as microbially enhanced oil recovery (MEOR), is to increase recovery of the original subsurface petroleum. MEOR processes typically use microorganisms to: (1) alter the permeability of the subterranean formation by blocking reservoir porethroats to divert injected water flow to regions still saturated with oil, (2) produce biosurfactants which decrease petroleum/water interfacial tensions and mediate changes in wettability releasing oil, (3) produce polymers which facilitate increased mobility of petroleum in the reservoir, (4) produce low molecular weight acids which cause rock dissolution and increase permeability, and (6) generate gases (predominantly $CO_2$) that increase formation pressure and reduce oil viscosity when dissolved in the oil.

Numerous microorganisms have been proposed for achieving various microbial objectives in subterranean formations. Most MEOR techniques involve injection and establishment of an exogenous microbial population in the oil-bearing formation. The population is supplied with growth substrate and mineral nutrients as additives to the waterflood used for secondary oil recovery. The growth of exogenous microorganisms is often limited by the conditions that prevail in the formation. Physical constraints, such as the small and variable formation pore throat diameters together with the high temperatures, salinities and pressures of fluids in the formation and the low concentrations of oxygen in the formation water severely limits the types of microorganisms that can be injected and that will thrive in the formation. Biological constraints, such as competition from indigenous reservoir microbes, the inherently adverse environment of subsurface reservoirs and the stress of changing environment from surface to reservoir also act to limit the viability of exogenously supplied microorganisms. To overcome these problems, indigenous reservoir microorganisms, commonly anaerobic organisms, have been proposed for use in MEOR techniques.

Microorganisms are commonly present in petroleum reservoirs cooler than about 80° C. (Bernhard and Connan, 1992; Magot et al., 2000; Orphan et al., 2000; Wilhelms et al., 2001). Biodegradation of petroleum, both crude oil and natural gas, in the subsurface is a common process (Connan, 1984; James, 1984; Horstad and Larter, 1997; Wenger et al., 2001; Head et al., 2003 and refs therein). With appropriate environmental conditions and sufficient time, indigenous bacteria and archaea can convert petroleum or other fossil fuels such as coals to methane over long geological time periods in the subsurface (Scott et al., 1994; Head et al., 2003; Roling et al., 2003 and refs therein). Methanogenesis, an exclusively anaerobic process, is commonly associated with biodegraded petroleum reservoirs. Methane containing isotopically lighter carbon is frequently found admixed with thermogenic methane (Scott et al., 1994; Larter et al., 1999; Sweeney and Taylor, 1999; Pallasser, 2000; Masterson et al., 2001; Boreham et al., 2001; Dessort et al., 2003) and methanogens represent common indigenous members of petroleum reservoir microflora (Mueller and Nielsen, 1996; Nilsen and Torsvik, 1996; Nazina et al., 1995 a,b; Ng et al., 1989). The methanogens described are those that reduce carbon dioxide to methane with few reports of acetoclastic methanogens from petroleum reservoirs (Obraztsova, 1987). Radiotracer experiments indicate that carbon dioxide reduction to methane is more prevalent than acetoclastic methanogenesis (Mueller and Nielsen, 1996; Rozanova et al., 1995) and high pressures in petroleum reservoirs favour net volume reducing reactions such as methanogenesis from carbon dioxide reduction (Head et al., 2003). The conversion process is slow under most geological conditions and it has been shown that typically it takes many millions of years to naturally biodegrade oil in a reservoir (Larter et al., 2003). In addition it has been shown, that degradation is often anaerobic in nature and that methane is often the natural end product of oil degradation (Larter et al., 1999; Head et al., 2003) with a significant proportion of the methane produced being associated with the reduction of carbon dioxide using secondary sources of hydrogen (Röling et al. 2003). Recent developments in microbiology have also demonstrated the existence of microbial consortia which can directly convert hydrocarbons to methane under conditions likely to be found in petroleum reservoirs (Zengler et al., 1999; Anderson and Lovely, 2000).

The first order kinetic rate constants of biodegradation of hydrocarbons and non-hydrocarbons in petroleum reservoirs under natural conditions has been shown to be around $10^{-6}$ to $10^{-7}$/year (Larter et al., 2003; Head et al., 2003), approximately 10,000 to 100,000 times slower than anaerobic hydrocarbon degradation rates in shallow subsurface environments such as landfills or shallow aquifers. To commercially recover significant quantities of oil as methane in realistic timescales of months to years using microbial technologies, the inventors have shown that degradation of large fractions of an oil layer must be accelerated to near-surface rates of methanogenesis. FIG. 1 shows a computer simulation of oil biodegradation throughout an entire 26 m oil column where methanogenesis is occurring at the rates typical in a near surface landfill environment. 20% of the remaining oil in the reservoir is recovered in approximately 10 years.

Thus to produce commercial quantities of methane by microbial degradation of petroleum in reservoirs under anaerobic conditions, technologies for acceleration of methane generation rates are needed and the degree of enhancement required to achieve commercial rates of production must be defined.

U.S. Pat. No. 6,543,535 outlines a process for stimulating microbial activity in petroleum-bearing subterranean reservoir formations, comprising:
(a) analyzing one or more components of the formation to determine characteristics of the formation environment;
(b) detecting the presence of a microbial consortium within the formation;
(c) characterization of one or more microorganisms of the consortium, at least one of the consortium members being at least one methanogenic microorganism, and comparing the members of the consortium with at least one known microorganism having one or more known physiological and ecological characteristics;
(d) using information obtained from steps (a) and (c) for determining an ecological environment that promotes in situ microbial degradation of petroleums and promotes microbial generation of methane by at least one methanogenic microorganism of the consortium; and
(e) modifying the formation environment based on the determinations of step (d) to stimulate microbial conversion of petroleums to methane.

SUMMARY OF THE INVENTION

The present inventors have identified additional key steps to those described in U.S. Pat. No. 6,543,535 for the identification of reservoirs where stimulation of methane production is feasible, techniques for stimulation of methane production, for specific acts needed to prevent methane destruction by common reservoir microorganisms, means to distinguish methane-oxidizing archaea from related methanogens, as well as improvements in some of the steps described in U.S. Pat. No. 6,543,535 and the definition of new steps necessary for effective methane production.

They have also identified errors in U.S. Pat. No. 6,543,535 relating to the types of organisms that are applicable to this type of process and appropriate stimulatory interventions.

Accordingly, the present invention provides a process for stimulating microbial methane production in a petroleum-bearing subterranean formation, comprising:
(a) analyzing one or more components of the formation to determine characteristics of the formation environment;
(b) detecting the presence of a microbial consortium, comprising at least one methanogenic microorganism, within the formation;
(c) assessing whether the formation microrganisms are currently active;
(d) determining whether the microbial consortium comprises one or more methanotrophic microorganism;
(e) characterization of one or more microorganisms of the consortium, at least one of the members of the consortium being a methanogenic microorganism, and comparing the members of the consortium with at least one known microorganism having one or more known physiological and ecological characteristics;
(f) characterization of one or more methanotrophic microorganisms of the consortium (if present), and comparing the members of the consortium with at least one known microorganism having one or more known physiological and ecological characteristics;
(g) using information obtained from steps (a) through (e) for determining an ecological environment that promotes in situ microbial degradation of petroleum and promotes microbial generation of methane by at least one methanogenic microorganism of the consortium;
(h) using information obtained from steps (a) and (f), if methanotrophic microorganisms are present, for determining an ecological environment that demotes in situ microbial degradation of methane by at least one methanotrophic microorganism of the consortium; and
(i) modifying the formation environment based on the determinations of steps (g) and (h), if methanotrophic microorganisms are present, to stimulate microbial conversion of petroleums to methane while minimising methane destruction by adverse processes.

It is preferred that the method includes as part of step (b) the step of detecting the presence of anaerobic oil-degrading bacteria.

This method includes the steps of identifying whether oil layers are capable of active degradation with indigenous organisms or introduced organisms, whether methanotrophic microorganisms that degrade methane produced by the methanogenic microorganisms are present, and if they are present, modifying the formation environment to reduce their activity.

The process of this invention stimulates and sustains the activity of a mixture of different microorganisms in a petroleum-bearing, subterranean formation to convert petroleum to methane, which can be produced. It also reduces the activity of methanotrophic organisms that may be present, to avoid the degradation of the methane produced and permits avoidance of processes other than methanogenesis that may act as alternative electron sinks and thus prevents methane production. While not wishing to be bound by theory, it is believed that a mixture of microorganisms converts petroleums to methane in multiple acts as follows:
(1) Microbial consortia degrade various petroleum compounds (e.g., saturated and/or aromatic hydrocarbons, asphaltenic, and nitrogen-sulphur-oxygen bearing organic compounds) into various compounds, which may include amines, alcohols, organic acids, and gases.
(2) Methanogens convert various low molecular weight compounds, which may include amines, alcohols, organic acids, and gases, into methane, $CO_2$, and water.

The present inventors have identified a third group of microorganisms in petroleum reservoirs, methanotrophic archaea, which convert methane into $CO_2$ and water.

The microorganisms naturally present in a subterranean formation will typically comprise multiple, mixed consortia of microorganisms, which will often depend on each other. For example, in the degradation of petroleum, syntrophic organic acid- and hydrogen-producing microorganisms obtain energy from petroleum degradation if their metabolic waste products (such as organic acids, acetate, and $H_2$) are continuously removed and maintained at a low concentration. Methanogenic microorganisms perform part of this waste-removal function by converting at least some of the waste products (for example, acetate, $CO_2$ and $H_2$) to methane. Methanotrophic archaea which typically exist in association with bacteria capable of utilizing intermediates of anaerobic methane oxidation, are capable of destroying any methane produced. This may occur either in proximity to or more distant from the site of methane formation. Knowing the distribution, abundance and activity of such methanotrophic archaea is essential for predicting the net yield and rate of methane production as a result of interventions to stimulate methanogenesis.

This description of one embodiment of the invention will focus on converting petroleum to methane in a conventional oil-bearing formation. However, the process of this invention can be applied to any petroleum-bearing formation in which environmental conditions can be modified to stimulate growth of at least one petroleum-degrading microorganism and of at least one microorganism that is capable of converting the degradation products to methane. The process of this invention can be used to stimulate microbial activity in oil shale deposits, newly worked and abandoned coal seams, tar sands and other fossil fuel deposits to transform the petroleum contained therein to methane. As used in this description, the term "fossil fuels" is used in a broad sense to include solid carbonaceous deposits such as kerogen, peat, lignite, and coal; liquid carbonaceous deposits such as oil; gaseous hydrocarbons mixtures containing components other than methane alone; and highly viscous petroleum deposits such as bitumen and tar.

This process of the invention can also be applied to reclamation projects where petroleum-contaminated soils and aquifers can be treated to enhance microbial conversion of petroleum to recoverable methane.

In this description, indigenous microorganisms that transform petroleum to methane are identified and then stimulated, whilst indigenous microorganisms that degrade methane or compete with methanogens for electron donors are identified and then suppressed.

The term "microorganisms" is intended to include bacteria and archaea, their enzymes, and other products as well as relevant eukarya. It will be understood that bacteria and archaea are representative of microorganisms in general that can degrade petroleum and/or convert the resulting products to methane under anoxic conditions.

ANALYZING THE FLUID/ROCK CHEMISTRY AND MICROBIOLOGY

Figure 1:
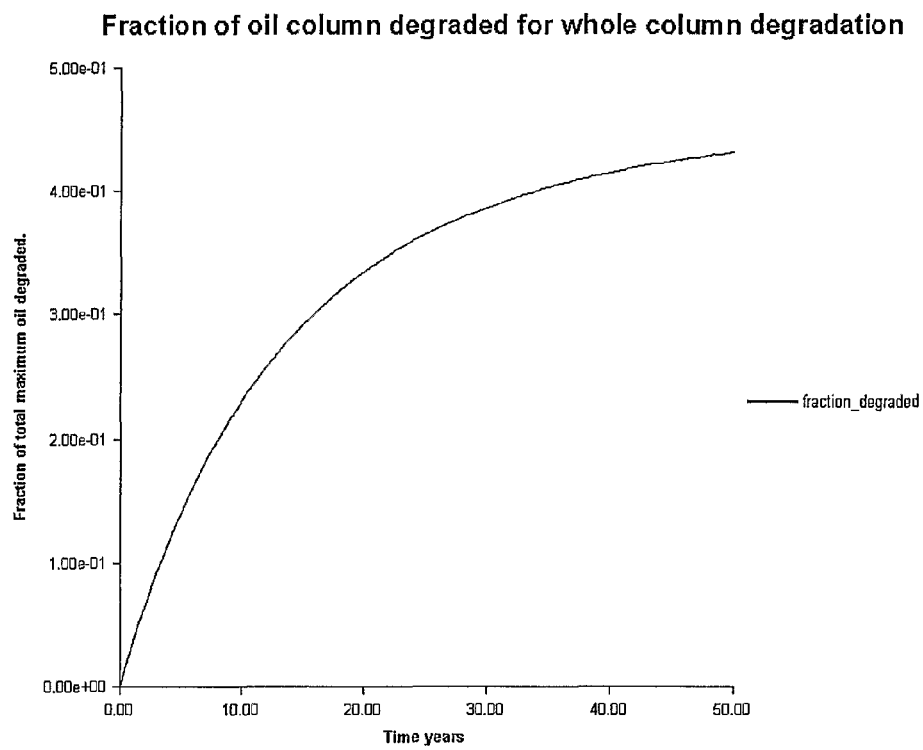
FIG. 1 shows a computer simulation of the extent of biodegradation and methane production throughout an entire oil column.

In practicing the process of this invention, the first step is to analyze one or more samples of fluids (waters, oils and gases) and rocks in the petroleum-bearing formation in which microbial activity is to be stimulated. While one sample is sufficient to practice the invention, multiple samples may be obtained.

Collecting Samples

The samples can be obtained by sampling procedures that are known to those skilled in the art. Normally, a fluid (liquid or gas) sample is retrieved from the formation through perforations in a well casing or from an open-hole test. The fluids can be sampled either downhole with a wireline formation fluid tester or fluid sampler or at the surface wellhead from a subsurface test, such as drill stem tests, production tests, or normal production. Both formation water and petroleum (oil and gas) samples are useful for evaluation of the formation environment. Rock samples can be retrieved from drill cores, cuttings, produced sediments and/or outcrop sites or rock data can be secured by interpretation of well logs or other techniques.

Environmental Analysis

An analysis of the formation's environment provides crucial information in determining suitable microbial growth stimulants or in situ environmental conditions for microbial activity. This analysis preferably includes determining the formation's temperature and pressure, which can be obtained in any suitable manner. While many reservoirs contain biodegraded oils, not all reservoirs contain currently active microbial populations. A key part of the process is the definition of reservoirs that contain relevant active organisms which can be accelerated to recover economic levels of methane through oil biodegradation.

To determine the environment in the reservoir, a geochemical analysis can be made of one or more fluids of the formation, such as formation water and petroleum, and/or one or more solids of the formation, which analyses are familiar to those skilled in the art. Preferably, the analysis is made of fluid and/or rock samples obtained from the formation. The fluid analysis can include measurement of the state values (for example, temperature and pressure) as well as a geochemical analysis of the formation water which can include assay for major anions and cations, pH, oxidation potential (Eh), chloride, sulphate, phosphate, nitrate, ammonium ion, salinity, selenium, molybdenum, cobalt, copper, nickel, and other trace metals.

The geochemical analysis will preferably also identify by-products that are known to be produced by indigenous microbial activity. For example, presence of methane, $CO_2$, RNA, DNA, enzymes, and carboxylic acids can be indicative of microbial activity and methane relatively depleted in the carbon 13 isotope is frequently found in oilfields where natural methanogenesis has occurred. In particular, anaerobic hydrocarbon degradation metabolites, such as alkyl and aryl substituted succinates or reduced naphthoic acids, are critical markers of systems in which the anaerobic degradation of hydrocarbons is taking place. The identification of such markers can be used as a first step in determining the presence of active anaerobic petroleum degrading microbial consortia.

A number of laboratory studies using aliphatic, aromatic, and polycyclic aromatic hydrocarbons as substrates for a variety of sulfate-reducing, denitrifying and methanogenic cultures have identified alkyl and aryl succinates, formed by the addition of fumarate either to a sub-terminal carbon of an alkane or to an alkyl substituent of an aromatic hydrocarbon, as the initial relatively stable metabolite in the degradation process (Widdel and Rabus, 2001; Rabus, et al., 2001; Wilkes, et al., 2002). Succinates have also been reported as metabolites from the biodegradation of both saturated and aromatic hydrocarbons in anoxic zones of petroleum-contaminated aquifers (Beller, et al., 2002). A recent study of an anoxic zone in an aquifer contaminated with gasoline has also identified 2-naphthoic acid and reduced 2-naphthoic acids as evidence of anaerobic degradation (Annweiler, et al., 2002). Aitken, et al. (2002) have shown that actively degrading oilfields were found to contain 2-naphthoic acid and, more significantly, amounts of reduced 2-naphthoic acids, such as 5,6,7,8-tetrahydro-2-naphthoic acid, which are exclusively indicators of anaerobic hydrocarbon degradation under the conditions appropriate for methanogenesis. The presence of such compounds is indicative of anaerobic degradation conditions appropriate for methanogenesis.

Other compounds which are indicative of active methanogenesis under indigenous conditions are archaeols, lipid molecules characteristic of archaea and which the inventors have identified in oilfields and coal mines undergoing active biodegradation. Archaeols characteristic of methanogens indicate active methanogenesis. Specific phospholipids and microbial DNA characteristic of methanogenic archaea can also be used to positively identify fields with active methanogenic processes that are capable of acceleration to commercial rates of methane production. In addition methanogens contain novel co-factors such as $F_{430}$, a nickel porphyrin associated with methyl coenzyme M reductase. A similar, but distinct nickel porphyrin with a higher molecular weight is associated with anaerobic methane oxidizing archaea, analysis of these will provide vital information on the relative prevalence and location of methanogens and methane-oxidizing archaea (Krüger, et al., 2003).

An important feature of these analyses is that they should be focused on the oil-water transition zones in reservoirs. The inventors have shown that specific indicators of active degradation have been shown to be preferentially concentrated in samples near petroleum/water contacts and it is here that sampling and characterisation should be targeted.

Actively degrading petroleum reservoirs can also be identified by several geochemical proxies. Elevated carbon dioxide levels in produced gases, isotopically distinct methane enriched in the carbon 12 isotope, acidic metabolite markers as described above and crucially by the detection and measurement of compositional gradients in the oil column. Gradients in oil columns such as variations in the saturated hydrocarbon contents versus depth in the oil layer have been detected in several oilfields by the authors and these have been used to assess the indigenous rates of hydrocarbon metabolism by reservoir microorganisms. The gradients are produced when organisms destroy hydrocarbons at the base of an oil column and the compositional profile of the oil column changes in response to this to produce a vertical and or lateral gradient in composition in such parameters including but not limited to saturated hydrocarbon content, n-alkane distribution or content or in the distribution of more resistant compounds such as isoprenoid alkanes or hopanes. The detection of such gradients can be used to identify fields where methanogenesis can be accelerated, as organisms are active where gradients are present. The rate of biological activity can be calculated from the gradient and thus indicate the extent to which acceleration of natural rates of degradation and methanogenesis are required. This can be used to assess the extent of additive treatments necessary for enhancement of methanogenesis to desired rates.

It is not only organic geochemical signatures that give indications of active processing of the oil naturally by microorganisms. High concentrations of metals such as cobalt, nickel or iron in the oils in the vicinity of the oil water contacts in the fields column are commonly found in reservoirs where active biodegradation has occurred and may be occurring.

Petroleum analyses will include quantitation of the major hydrocarbon types such as saturated hydrocarbons, aromatic hydrocarbons, resins and asphaltenes and detailed molecular characterisation of the specific hydrocarbon fraction such as n-alkanes, isoprenoid alkanes, alkylbenzenes, alkylnaphthalenes and so on. Petroleum analyses of oil and gas will aid in identifying the abundances and compositions of the different carbon substrates for the microorganisms. While in principal many of the components of crude oils can be used for methanogenesis the most reactive oils and the fields most suitable for methanogenic conversion will still contain abundant n-alkanes, isoprenoid alkanes and other more reactive components such as light alkanes and aromatic hydrocarbons. Analysis of petroleum extracted from produced fluids or cuttings or core samples taken through the oil column will allow chemical analyses to define the extent of any compositional gradients that exist in the oil column. Determination of the compositional gradients can be used to determine the current rates of biodegradation of the oil column and thus the extent to which biodegradation rates and methanogenesis rates in particular need to be accelerated.

The rock analysis may include mineralogical, chemical and facies descriptions as well as measurements of formation properties such as porosity, permeability, capillary pressure, and wettability.

Analysis of the reservoir geological environment should preferably be carried out using geophysical and geological mapping procedures. The inventors have shown that the relative volumes and spatial arrangements of oil layers and water layers control the net rates of biodegradation (Larter, et al., 2003). Oil zones adjacent to or surrounded by reservoir zones saturated with water will be most optimal for stimulation. Residual oil zones with high water saturations will be very favourable environments for stimulation.

Microbial Analysis
Collecting Indigenous Microorganisms

Correct sampling is a vital element of these analyses. Microbial populations in deep subsurface environments are typically very low and on the order of five to six orders of magnitude less abundant than in near-surface sediments (ca. $10^3$ to $10^4$ cells per cubic centimetre in the deep subsurface). Thus to avoid misidentification of contaminant organisms as indigenous, it is essential that stringent contamination control measures are adopted. Treatment of all reagents and materials, except amplification primers, with UV and enzymatic treatment with DNase I is essential when nucleic acid based analyses are conducted. Samples for nucleic acid analysis should also be frozen immediately or fixed by addition of filtered 50% ethanol. Subsamples should be taken from the centre of whole cores under sterile conditions to avoid contamination from the exterior of the core contaminated during drilling. Samples for cultivation based studies should be stored either chilled or at close to in situ temperatures to reduce the growth of contaminating microorganisms during storage and transport. Ideally samples should be of core material to increase the likelihood of obtaining indigenous organisms free from contaminants however formation water and/or drill cutting samples may be analyzed for the presence of active microorganisms if conditions are maintained to inhibit exogenous contaminant organisms while promoting those adapted to in situ conditions. Microorganisms in water samples are preferably concentrated by filtration and/or centrifugation before the analysis is performed. The amount of the indigenous microbe population will typically be a small fraction of the sample's volume. In a typical oil-bearing formation, water may contain less than 0.025 mg of microorganisms per liter. Microorganism concentrations can be amplified to facilitate detection using conventional microbial detection techniques, which are familiar to those skilled in the art. Incubation of samples in microcosms that replicate as much as possible in situ conditions to identify factors that promote or inhibit particular metabolic processes is also a key approach to identifying candidate petroleum systems for successful microbial stimulation.

Characterizing the Indigenous Microorganisms

Microorganism characterization as used in this description means identifying the key characteristics of a microorganism or consortium of microorganisms using one or more of the following methods: biochemical methods, physiological methods, biogeochemical process measurements, optical methods, or genetic methods. The degree of similarity between these key characteristics of sampled microorganisms and microorganism with known properties can be used to establish identity and infer the physiology, metabolic functions, and ecological traits of the sampled microorganisms by techniques well established in the field of microbial ecology (for example see, Head et al., 1998; Head, 1999; Gray and Head, 2001; Röling & Head, 2004; Stahl, 1997); Trüper and Schleifer, 1992)

Non limiting examples of characterization methods that can be used in the process of the invention include:

(a) Enrichment culture techniques to obtain microorganism isolates from which key biochemical, morphological, physiological, ecological, and genetic traits may be determined and compared against the traits of known microorganisms.

(b) Determination of the phospholipid fatty acid composition (PLFA) of the indigenous microorganisms and comparison with PLFA distributions of known microorganisms.

(c) Determination of isoprenoid glyceryl ether distributions (archaeols) characteristic of methanogenic archaea and comparison with isoprenoid glyceryl ether distributions of known microorganisms.

(d) Compound-specific isotope analysis to identify organisms utilizing methane.

(e) Characterization of specific nickel porphyrins to distinguish methanogenic and methane-oxidizing archaea.

(f) Genetic characterization methods, of which two non-limiting examples (among many) are listed below:

1. Sequences of genetic fragments from sampled microorganisms including but not restricted to 16 S rRNA genes (bacterial, archaeal) genes encoding the alpha subunit of methylcoenzyme M reductase (mcrA) from methanogenic and methane-oxidizing archaea and genes encoding the alpha-subunit of benzylsuccinate synthase (bssA) and homologues, involved in the initial activation of hydrocarbons by anaerobic hydrocarbon degrading bacteria. These are compared against nucleic acid sequences from known microorganisms (for example, using the Ribosomal Database Project, Michigan State University, East Lansing or the Genbank database at the National Center for Biotechnology Information located in the National Library of Medicine (Building 38A Room 8N805), Bethesda, Md. 20894, U.S.A.) to establish the phylogenetic identity with nearest known relatives using established techniques (Röling & Head, 2004).

In particular, quantitative analysis of these target genes characteristic of particular organisms or processes that must be controlled for maximizing recovery of methane (e.g. using real-time PCR) is of use, as is the design of specific primers that can be used to distinguish and quantify the key variants of mcrA involved in methanogenesis and methane-oxidation respectively and for quantification of potential primary hydrocarbon-degrading syntrophs.

The present inventors have determined the presence of particular microorganisms in petroleum reservoirs that are significant targets for these analyses. These include methane oxidizing archaea, methanogens and anaerobic hydrocarbon-degrading bacteria. 16 S ribosomal RNA sequences of methane oxidizing archaea that must be controlled to maximise methane recovery, have specifically been identified in biodegraded petroleum reservoirs.

The following sequences were amplified with the specified primers from samples extracted from a biodegraded petroleum reservoir. The closest matching sequences in database searches are provided for information. The sequences are detailed in Annex 1.

| Clone | Closest Match | Identity (%) |
|---|---|---|
| Sequences amplified with primers Arch46 and Arch1017 (ca. 850 bp) | | |
| ATS29A SEQ ID: 2 | EM_PRO: AB050224.1 Uncultured archaeon SAGMA-S | 84.642 |
| ATS29C SEQ ID: 3 | EM_PRO: AB050225.1 Uncultured archaeon SAGMA-T | 84.309 |
| ATS10C SEQ ID: 1 | EM_PRO: AB050224.1 Uncultured archaeon SAGMA-S | 84.078 |
| Sequences amplified with primers Arch344 and Arch855 (ca. 490 bp) | | |
| ATS17a SEQ ID: 5 | UAR305083 Uncultured archaeon 63-A23 partial 16S rRNA gene, clone 63-A23; Schaefer H., Ferdelman T. G., Fossing H., Muyzer G.; "Microbial diversity in sediments of the Benguela Upwelling System showing anaerobic methane oxidation"; Unpublished | 98.616 |
| ATS13b SEQ ID: 4 | AY053468 Uncultured archaeon AT425_ArB9 16S ribosomal RNA gene; Lanoil B. D., Sassen R., La Duc M. T., Sweet S. T., Nealson K. H.; "Bacteria and Archaea physically associated with Gulf of Mexico gas hydrates"; Appl. Environ. Microbiol. 67(11): 5143-5153(2001) | 92.668 |
| ATS21c SEQ ID: 6 | UAR305083 Uncultured archaeon 63-A23 partial 16S rRNA gene, clone 63-A23; Schaefer H., Ferdelman T. G., Fossing H., Muyzer G.; "Microbial diversity in sediments of the Benguela Upwelling System showing anaerobic methane oxidation"; Unpublished | 90.987 |
| ATS23a SEQ ID: 7 | AY053468 Uncultured archaeon AT425_ArB9 16S ribosomal RNA gene; Lanoil B. D., Sassen R., La Duc M. T., Sweet S. T., Nealson K. H.; "Bacteria and Archaea physically associated with Gulf of Mexico gas hydrates"; Appl. Environ. Microbiol. 67(11): 5143-5153(2001). | 93.081 |

Clones ATS17A (SEQ ID:5) and ATS29A (SEQ ID:2) have a unique approx. 40 bp insertion which indicates that they are distinct form previously identified organisms.

2. Oligonucleotides designed to hybridize to the 16 S rRNA genes of specific microorganisms and target genes indicative of key processes 10 (hydrocarbon activation, methane generation, methane oxidation) should be used in polymerase chain reaction-based methods. Although potentially applicable, the use of such oligonucleotide probes labeled with radioactive phosphorus, biotin, fluorescent dyes, enzymes and other suitable tags are likely to lack the sensitivity required for analysis of subsurface samples unless linked to amplification techniques such as the polymerase chain reaction or culture-based enrichment or analysis of microcosms.

The following paragraphs describe an application of DNA probes to identify the presence and identity of methanogens and methanotrophic archaea which must be promoted and inhibited respectively to achieve maximal methane recovery.

(i) Determining the presence and identity of methanogens and methane oxidizing archaea.

The conversion of petroleum to methane requires the active participation of methanogens. The presence of methanogens within the samples indicates the high likelihood of in situ methane formation. However, methane oxidizing archaea may also be present and these must be distinguished in order to design the most appropriate interventions to maximise methane production. 16 S rRNA genes and genes encoding the alpha subunit of methyl coenzyme M reductase can in principle be used to detect methanogenic archaea. U.S. Pat. No. 6,543,535 incorrectly asserts that "methyl reductase" (in fact methyl coenzyme M reductase) is unique to methanogenic archaea. Homologues of methyl coenzyme M reductase are also found in anaerobic methane oxidizing archaea (Krüger, et al., 2003; Hallam, et al., 2003) and thus oligonucleotide primers targeting regions which are conserved in methanogen mcrA genes and distinct in methane-oxidizer mcrA genes (Krüger, et al., 2003; Hallam, et al., 2003) must be designed to distinguish the two types of organism. Alternatively broad specificity mcrA primers must be used (e.g. Lueders and Friedrich, 2003) followed by cloning and sequencing of the mcrA genes sampled in order to determine their provenance.

Determining an Ecological Environment to Stimulate Petroleum Degradation and Methanogenesis and to Retard Methane Oxidation From knowledge of the indigenous microorganisms and their nutritional requirements, the chemical composition of the formation's oil, water and matrix rock, and the physical characteristics of the formation (pressure, temperature, porosity, saturation, etc.), the overall ecological environment needed to promote and retard the activity of appropriate members of the microbial consortium can be determined. This information is then used to modify environmental conditions in the formation's to promote microbial conversion of petroleum to methane and to prevent microbial degradation of methane.

Altering the activity of microorganisms in the subsurface depends on at least one of the following factors:

1) Adding and/or subtracting and/or maintaining key components required for microbial growth and/or activity as determined by the laboratory and/or in situ pilot studies; and
2) Controlling and/or maintaining the subsurface environment (for example, chemistry, temperature, salinity, and pressure).

Microbial Ecology

Figure 2:
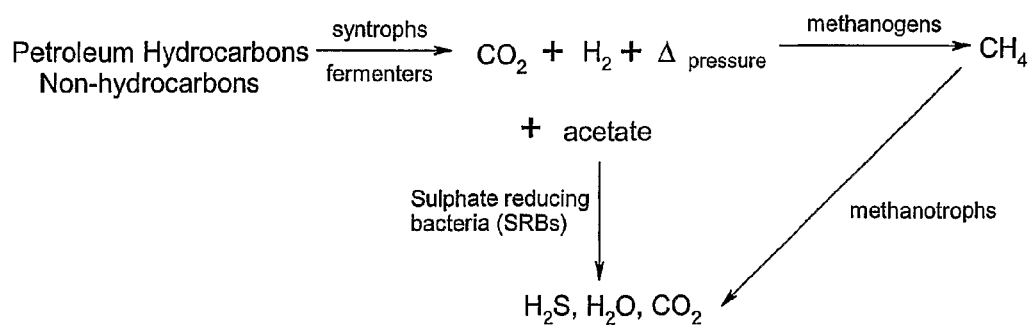
FIG. 2 shows the processes involved in methane production from petroleum.

In order to stimulate and/or sustain commercial rates of petroleum degradation and methane generation and to reduce the rate of methane degradation, basic components of the subsurface environment and microbiota are determined. The basic system active in petroleum reservoirs is shown in FIG. 2. To accelerate methane production it is necessary to accelerate the activity of syntrophs and methanogens while reducing methanotroph activity.

To convert petroleum to methane, the formation's indigenous microbial consortium may comprise petroleum-degrading microorganisms having similar genetic characteristics to one or more of microorganisms listed below. If hydrocarbon degrading iron-reducing, nitrate-reducing (including, but not exclusively, denitrifiers) sulphate-reducing bacteria and/or archaea are present, specific steps should be taken to inhibit their activity, otherwise hydrocarbons will be degraded to carbon dioxide and water without the formation of methane. Furthermore any aerobic hydrocarbon degrading organisms identified are unlikely to be indigenous to the formation. These too would be detrimental to the process of petroleum hydrocarbon conversion to methane. Such organisms will most likely be inactive unless substantial quantities of oxygen are provided. Potential syntrophic organisms that will convert complex organic carbon in petroleum into substrates that can be converted to methane by methanogens include organisms related to the following: *Syntrophobacter* spp., *Syntrophus* spp., *Syntrophomonas* spp., *Thermoanaerobacter* and relatives, *Thermotoga, Thermoanaerobacterium, Fervidobacterium, Thermosipho, Haloanaerobium, Acetoanaerobium, Anaerobaculum, Geotoga, Petrotoga, Thermococcus, Pyrococcus Clostridium* and relatives, and must also include methanogenic archaea of one or more of the orders Methanobacteriales, Methanomicrobiales, Methanosarcinales and relatives, Methanopyrales, and Methanococcales to convert degradation products to methane.

Organisms that may result in lower methane yields may also be present in the formation and must be identified. These will primarily be anaerobic methane oxidizing archaea. These have not been cultivated in the laboratory and are referred to as ANME-1 and ANME-2 which are related to but distinct from the Methanosarcinales. In addition to these two major groups of methane-oxidizing archaea other groups may be present. If present the activity of such organisms must be controlled to prevent reduction in methane production.

Understanding the subsurface ecology allows one skilled in the art to deduce likely additives that can stimulate subsurface activity. Additives could include (in an appropriate form for distribution throughout the formation) but are not limited to:

major nutrients containing nitrogen and phosphorus that do not accelerate competing processes such as nitrate or sulphate reduction, non-limiting examples may include $Na_2HPO_4$, $K_2HPO_4$, $NH_4Cl$ added via water injection or ammonia gas ($NH_3$), volatile phosphorus ($PH_3$, $CH_3$—$PH_2$) compounds added which can be quickly dispersed through the gas caps facilitating nutrient supply very quickly over large areas of the fields. Phosphates may precipitate chemically in formations and therefore less reactive forms of phosphorus such as polyphosphate and phosphorus pentoxide may be more appropriate additives; $NaNO_3$, $KNO_3$, $NH_4NO_3$ would accelerate the syntrophic components of methanogenic consortia however, methanogens exclusively use ammonium ion as a nitrogen source and addition of nitrate would stimulate nitrate reducing bacteria which would repress methanogenesis by more effective competition for electron donors. It is therefore vital that the correct form of nitrogen and phosphorus are added in order that processes that would inhibit methanogenesis are not fortuitously stimulated;

vitamins (non-limiting examples may include cyanocobalamine (vitamin $B_{12}$), folic acid, ascorbic acid, and riboflavin);

trace elements (non-limiting examples may include B, Zn, Cu, Co, Mg, Mn, Fe, Mo, W, Ni, and Se);

buffers for environmental controls;

waters of different salinities and pH values or containing complexing agents such as organic acids such as oxalate, EDTA or other multidentate ligand organic compounds, including hydroxylated acids, to facilitate mineral dissolution and release of natural nutrients including, but not limited to, potassium, ammonium or phosphate ion from dissolution of feldspars, clays or other silicates and carbonates.

U.S. Pat. No. 6,543,535 suggests that both natural and artificial electron acceptors (non-limiting examples may include $SO_4^{2-}$, $NO_3^{2-}$, $Fe^{+3}$, humic acid, mineral oxides, quinone compounds, $CO_2$, $O_2$, and combinations thereof) may be added to stimulate microbial activity. While these amendments will potentially stimulate microbial activity, all with the exception of $CO_2$ will be detrimental to methane generation from petroleum and should not be used if conversion of petroleum to methane is to be achieved. All of these electron acceptors will stimulate organisms that will outcompete methanogens for electron donors.

Additives may be used to accelerate methane production. For example, if cobalt or nickel is known to stimulate growth of the closest-matching methanogenic microorganisms, and if cobalt or nickel is present in the formation in only limited concentrations in a labile accessible form, then addition of these limiting components in an accessible soluble form to the formation should also stimulate the uncharacterized methanogens.

Suitable stimulants can be tested and optimized using indigenous microorganisms in laboratory microcosms, cultures or in situ pilot sites to determine their effectiveness at promoting rapid petroleum-degradation and methanogenesis. However, any stimulants chosen should also not increase the rate of activity of any methanotrophic or nitrate, iron or sulphate reducing microorganisms that will suppress methanogenesis by competition for common electron donors. If such organisms are stimulated their activity should be independently blocked.

Indigenous microbial consortia are grown in nutrients using a range of nutrient media, with varying pH, salinity, trace metals, to find those conditions which support high rates of petroleum degradation linked to methanogenesis and low rates of methane degradation. These microcosm and culture studies will typically involve several cycles of stimulant addition and stimulant combinations as well as varied environmental conditions (e.g. salinity, temperature, pH see below). Because the indigenous microorganisms found in a given formation and the chemistry of the formation fluids and formation rocks will typically be unique to that formation, the conditions for promoting growth of indigenous microorganisms may vary from one petroleum accumulation to another and may vary from one location in the petroleum accumulation to another. Conditions favourable for microorganism growth in part of the petroleum accumulation may not be optimum for another part of the petroleum accumulation. In addition it may be necessary to inhibit methane-oxidizing archaea that are present in locations that are removed from the site of methane generation to minimise loss of methane during extraction.

The inventors have concluded that hydrocarbon degradation in deep subsurface petroleum reservoir environments is often phosphorus, potassium or nitrogen limited. In pivotal studies, Bennett and co-workers (summarized in Bennett et al., 2001; Rogers and Bennett, 2004 and references therein) have shown a close relationship between the geomicrobiology of petroleum-contaminated aquifers, mineral alteration and groundwater chemistry. Biological activity perturbs general groundwater chemistry and therefore mineral-water equilibria, and at the microscale, attached organisms locally perturb mineral-water equilibria, releasing limiting nutrients. In an oil-contaminated aquifer, it was shown that feldspars weather exclusively near attached microorganisms in the anoxic region of the contaminant plume and that indigenous bacteria colonized feldspars that contain potassium or trace phosphorus. Most phosphorus in many petroleum reservoirs and reservoir encasing sediments is in feldspars and it has been suggested that natural feldspar dissolution in some oil reservoirs (e.g. the Gullfaks field in the North Sea) is related to biodegradation of the associated oils (Ehrenberg and Jacobsen, 2001). Phosphorus contents of oils are low (approximately 1 ppm or much less) whereas phosphorus contents of sandstone reservoirs or reservoir encasing shales are much higher (up to 1000 ppm or more of oxide equivalents). The phosphorus is thus generally present in mineral phases of low water solubility. Indeed, the inventors believe, without wishing to be bound by theory, that supply of limiting nutrients from mineral dissolution in reservoirs or reservoir encasing shales in many instances may be the rate-limiting step in subsurface petroleum biodegradation. Addition of phosphorus as soluble forms of phosphates in injected waters or alteration of reservoir water chemistry by change of pH, salinity or addition of complexing agents including organic acids or multidentate organic chelating agents can be used to release available phosphorus or potassium to accelerate petroleum biodegradation. Ammonium phosphate or potassium ammonium phosphate would add both essential nitrogen and phosphate and also potassium.

The present inventors have determined that concentration of ammonium ion ($NH_4^+$) in the formation waters is also critical to the rate of methanogenesis. Naturally in petroleum reservoirs mean concentrations of ammonium ion range from a few ppm up to a up around 500 ppm but are typically around a few tens of ppm (Manning and Hutcheon, 2004). In contrast in near surface anoxic environments (e.g. landfills) concentrations of ammonium ion range up to over 1000 ppm. Nitrogen supplied in the form of ammonium ion will accelerate methanogenesis whereas if supplied as nitrate, competitive nitrate dissimilatory reduction will eliminate or reduce methane production.

In sandstone reservoirs, reservoirs in which petroleum is trapped in the pore systems of sandstones, the present inventors have determined that the concentration of nutrients such as phosphorous is rate limiting on overall oil biodegradation rate and methanogenesis. The concentration of phosphorous may be increased by the addition of exogenous phosphorous, or by release of phosphorous from the reservoir matrix by modifying the characteristics of the reservoir waters such that the phosphorus containing minerals in the reservoir such as clays or feldspars dissolve releasing their phosphorus. For example injection of fresh, low salinity waters or acidic waters will aid in feldspar dissolution releasing nutrients. Addition of organic acids such as oxalate, EDTA, citrate or other multi-ligand chelating agents including hydroxylated acids and other multi functional chelators would facilitate mineral dissolution and release of natural phosphorus and other essential nutrients from reservoir minerals. These treatments may stimulate all microorganims present, not only those required for conversion of petroleum to methane. To prevent the activity of organisms that will outcompete methanogens for electron donors certain amendments may be required to suppress their activity. These may include (but are not limited to) sodium molybdate (or other hexavalent cation) to inhibit sulphate-reducing bacteria and sodium chlorate to inhibit nitrate reducing bacteria. Methane-oxidizing archaea are unlikely to be active at the site of methanogenesis but if present in other regions of the formation, should be inhibited. The fact that these groups of archaea are likely to be spatially separated is important since the known inhibitors of anaerobic methane oxidation (e.g. bromoethane sulfonic acid) also inhibit methanogens. In addition methane-oxidizing archaea often exist in close association with sulphate-reducing bacteria that consume the products of anaerobic methane oxidation driving methane oxidation to completion. This permits anaerobic methane oxidation to be inhibited with inhibitors of sulphate reduction such as sodium molybdate.

Formation Conditions

Environmental conditions in petroleum bearing, subterranean formations may not be conducive to thriving populations of the appropriate indigenous microorganisms. The appropriate microorganisms may need to be stimulated to be more active. This stimulation is carried out by modifying one or more parameters of the formation environment. For example, high-salinity environments may greatly slow the rates of petroleum degradation and methanogenesis. Introduction of low salinity waters may stimulate the degradation and methanogenesis activity.

Equally, the environment may also be altered to slow the rate of methane degradation. Ideally, the changes required to increase the rates of petroleum degradation and methanogenesis will simultaneously decrease the rate of methane degradation.

The present invention can be practiced in any petroleum-bearing formation that is suitable for microbial life or that can be modified to be suitable for microbial life. In general, the formation fluids will have a temperature less than about 130° C., a pressure less than about 10,000 psig (6895 kPa), a subsurface pH between about 3 and 10, and a salt concentration less than about 300,000 parts per million. Reservoirs cooler than 80 degrees centigrade or which can be cooled to below 80 centigrade are the optimal reservoirs for treatment. The inventors have shown that indigenous organisms are not likely to be active in reservoirs hotter than 80° C. or where geochemical and geological data indicate the reservoir has ever been heated to more than 80° C. (Wilhelms, et al., 2001). In these circumstances injection of exogenous methanogenic consortia will be necessary.

Formation environmental parameters of principal concern for providing optimal petroleum degradation and methanogenesis conditions include, but are not limited to, temperature, salinity, pH, alkalinity, organic acid concentration, nutrients, vitamins, trace elements, availability of terminal electron acceptors (high levels will suppress methane generation), and toxic substances (to suppress the activity of competing microorganisms). One or more of these environmental parameters may require adjustment or maintenance within specific ranges to initiate or sustain commercial rates of methane generation.

The environmental conditions for promoting growth of a microbial consortium in a formation will necessarily involve many factors including, without limiting the scope of this invention, the following, either alone or in combination:
  changes in the formation temperature, pH, Eh, mineralogy, and salinity and the concentrations of $CO_2$, $O_2$, and $H_2$ in the formation; and
  creation, movement and/or maintenance of water oil interfaces between different petroleum-degradation microbial populations, and/or microbial methanogenesis zones.

Modifying the Formation Environment (Adding Stimulants, Depressants and/or Changing Environmental Factors)

The additions of stimulant(s), inhibitor(s) or change(s) of environmental factor(s), either alone or in combination, are referred to in this description as microbial growth "modifiers". The particular modifier, or combination of modifiers, suitable for a particular application will depend on the microbial consortium to be modified and the formation environmental conditions. Since indigenous microorganisms are typically in a nutrient deprived state, one stimulation strategy will typically involve addition of a nutrient. However, since stimulating methane production is also likely to stimulate methane degradation, the modifier package will often contain an inhibitor for methane degradation activity (see comments above). Once a modifier package is determined, the formation environment can be altered on a continuing basis or discontinued after a suitable period of time to permit change in the populations of the microorganisms depending on assessment of environmental analyses of the producing reservoir.

As mentioned above, in fields where there is no activity of the indigenous microorganisms, the addition of exogenous microorganisms will be necessary. These may also be term "modifiers".

Injection Process

For growth or activity modifiers that involve injecting a material into the formation, the material can be added to a fluid flood such as an aqueous solution or gas (such as $CO_2$) or solvent or polymer that is injected into the formation by any procedure found most convenient and the invention is not limited to any particular process of introducing the stimulants. The implementation of the present invention will often involve adding the stimulant package by a waterflood program. To simplify the following discussion, the above-identified injection carrier will be referred to as water.

Microbial stimulants or reservoir treatments can be added to water and injected into the formation through one or more injection wells and pumped to flow toward one or more production wells. Underground oil formations are frequently flooded with water in order to supply additional pressure to assist oil recovery. The microbial stimulant is preferably injected into a well as part of the injection program of the waterflood.

The amount of water introduced into the formation and the amounts of microbial modifiers contained in the water will depend upon the results desired. Those skilled in the art can determine the amount needed to provide methane production based on the teachings of this description.

Multiple modifiers can be injected into the formation together or in separate injection steps. For example, a slug or bank of water carrying one modifier may be followed by a second slug or bank of water carrying a second modifier. Another example may include alternately injecting one water bank followed by a gas injection step. In addition stimulants may be injected at one location to enhance methanogenesis whereas in some cases inhibitors may be injected at a different location on the gas extraction flow path to prevent detrimental processes such as methane oxidation. Injection of gas below the degrading oil column may facilitate circulation of waters and nutrients to the microorganisms and may also allow for injection of volatile microbially accessible nutrients which would disperse rapidly in any gas phase in the reservoir environment.

Layered reservoir bioreactors are the most feasible to implement for methane production and facilitated methane removal. In such a reservoir bioreactor, the biodegrading oil column and/or residual oil zones would be vertically segmented and the environments could be controlled, for example, in the following manner:
(a) A lower zone of degradation of oil or injected reactive organic substrates is environmentally modified to produce abundant free gas-usually methane and carbon dioxide.
(b) An upper zone of degradation of oil or injected reactive organic substrates is environmentally modified to produce abundant free methane.
(c) Free gas from the lower layer buoyantly moves up through the layered bioreactor and any free methane or methane in aqueous or oil solution partitions into the moving gas phase and is carried to the gas cap for production.

Gas flushing or sparging of degrading oil columns by injecting gas from a well or by producing gas in a biodegrading reservoir layer below the zone to be flushed could also be employed. A gas phase (methane, carbon dioxide, and air) could be injected below the degrading oil column. With methane and carbon dioxide simple partitioning would occur and remove methane as a free gas phase. With air, aerobic degradation of organic matter at the base of the column would facilitate pressure production and large volumes of gas (carbon dioxide) to carry up into an anaerobic zone where methane production was occurring.

Gas sparging or flushing of degrading oil or residual oil zones would facilitate introduction of nutrients either as entrained water soluble nutrients or via volatile gas transported nutrients. This would be a fast way of getting nitrogen, phosphorous and other nutrients to the methane production zones.

Gas sparged or flushed reservoirs or reservoirs operating without gas sparging ideally would have injector wells below the initial oil water contact (owc) to inject nutrients, inhibitors and metabolic modifiers into waters that would migrate up into the degrading oil zones as production proceeds.

Acceleration of methanogenesis, provision of nutrients, injection of organic matter-degrading microorganisms and production of gases (methane and carbon dioxide) can be facilitated by injection of reactive liquid organic matter into or below biodegrading oil legs. Organic matter may be from sewage, waste waters, biomass (e.g. liquid waste) and industrial chemical wastes and farm wastes among others. Such materials could be injected as part of a normal reservoir pressure maintenance program into actively degrading petroleum columns or into sterile petroleum reservoirs needing infection with organic matter degrading organisms.

To accelerate degradation of reactive organic matter such as sewage for gas production (in the form of carbon dioxide) and pressure production then $NaNO_3$, $KNO_3$, $NH_4NO_3$, would be suitable additives, though these should be avoided if methane production from such readily degradable organic substrates is desired.

Creation/Maintenance of Biodegradation Interfaces

Microorganisms in subterranean formations tend to be most active at environmental boundaries such as between fermentation zones and methanogenesis zones. Therefore, microorganism activity in a formation may be increased by increasing the number of such boundaries, which serve as environmental interfaces. U.S. Pat. No. 6,543,535 claims one method for increasing the number of environmental interfaces is to modify the water flood injection rates. A second method is to alternate or vary the injection modifiers into the formation to in effect create moving environmental fronts. A third method involves forming small-scale environmental interfaces by forming petroleum-water emulsions in the formation or by changing the clay chemistry. The present inventors consider that a very practical fourth method relies on knowledge of field geometry. The optimal fields for processing for methanogenesis are fields where already existing natural interfaces between water and oil are large. These include any fields with residual oil columns produced either naturally over geological time or via primary or enhanced recovery procedures.

The most optimal fields for recovery of oil as methane would be those fields that have large residual oil columns below the producible oil legs. A common process during field filling is movement of oil legs through field tilting, leakage of oil through seals and during the biodegradation process oil is naturally consumed and oil legs move upwards leaving a residual oil zone with large water/oil interfacial areas. The inventors have determined that the best fields for recovery of oil as methane such as the Troll field or Frigg field in the North Sea often have thick natural residual oil zones with high water saturations ideal for processing to methane through microbial activity (Horstad and Larter, 1997; Larter, et al., 1999). (FIG. 3)

Figure 3:
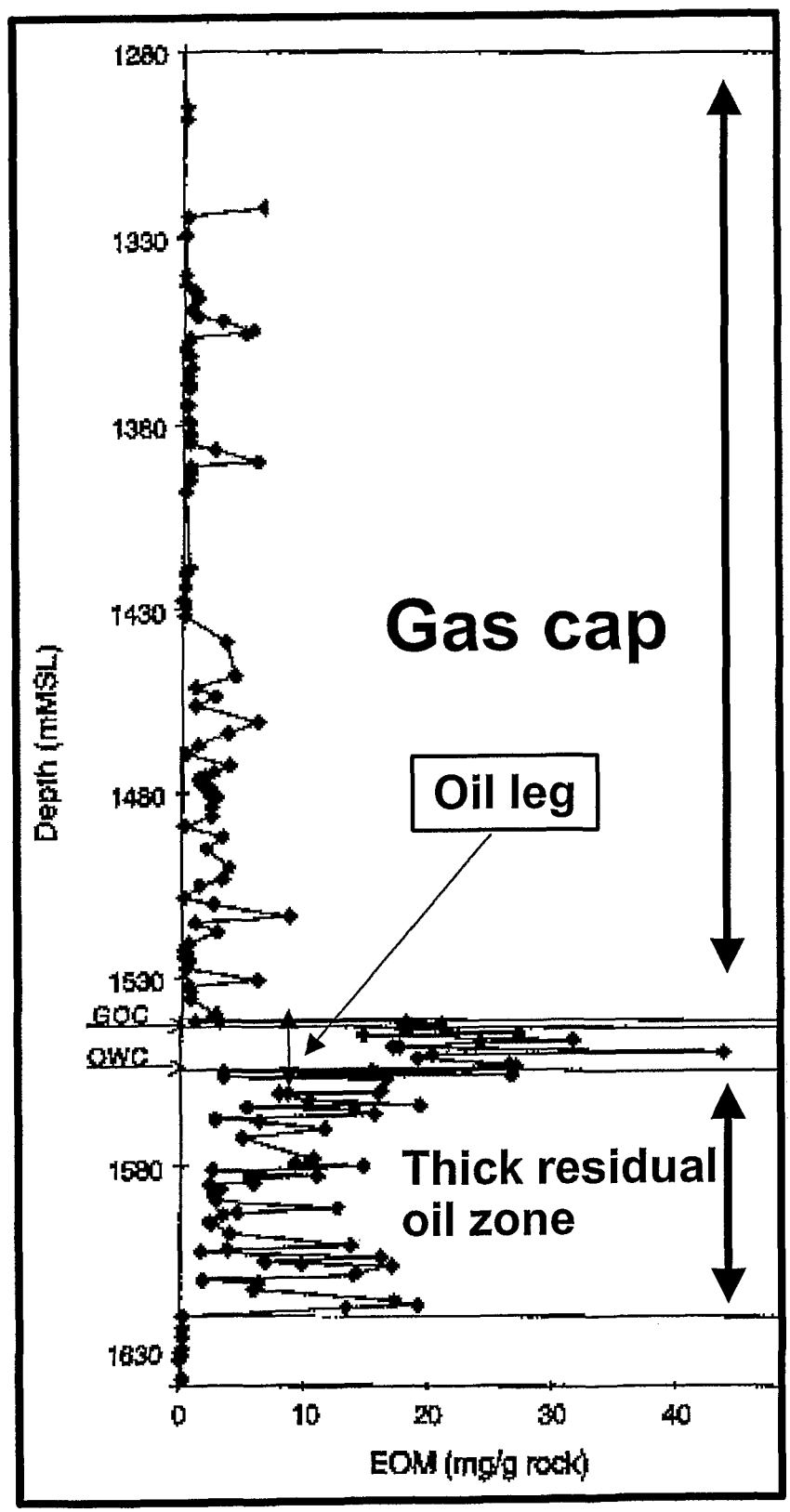
FIG. 3 shows an ideal configuration for an oil and gas field to recover both residual oil and producible oil as methane.

FIG. 3 shows an ideal configuration for a field to produce methane and recover both residual oil and producible oil as methane. The figure shows the oil yield as a function of depth for a large oil and gas reservoir in the North Sea (Troll field—after Horstad and Larter, 1997). Gas production from the gas cap would recover gas which is partly derived from microbial conversion of oil in the oil leg and residual oil zone to methane. As oil is produced from the oil leg water moves up into the residual oil zone and oil leg facilitating methanogenesis and oil recovery as methane by increase of oil/water surface area and addition of nutrients, metabolic modifiers or organisms under the oil leg.

Such high interfacial area zones can also be produced through normal recovery processes as oil legs are produced to leave a residual oil zone. Such dispersed oil zones are ideal for promotion of microbial activity as the water/oil interface is large facilitating easy transmission of nutrients, metabolic modifiers or organisms to the reaction sites in the oil leg.

Changing Environmental Conditions

Changing the environmental conditions for promoting growth of the microbial consortium in a formation can be accomplished by injection of material into the formation. Environmental factors that can be changed include formation temperature, pH, Eh, and salinity and the concentrations of $CO_2$, $O_2$, and $H_2$ as well as other electron donors and acceptors. As discussed above, the most likely process of environmental change will be by injection of fluids (e.g. water, solvent, and polymer) or gases as part of the secondary or tertiary recovery process.

The ideal location of injection wells is below the current oil water contacts or residual oil zones that migrate upwards during normal oil production or consumption of oil during biodegradation that allows the oil zone to move upwards facilitating movement of water through any residual oil remaining. This allows for modifying agents and organisms to be dispersed upwards into the remaining oils facilitating increased degradation rates and methane production.

As an example of changing environmental conditions, oil formation waters often contain low concentrations of indigenous phosphate ion which the inventors consider to be a rate controlling nutrient in most biodegrading reservoirs. Injecting water of very low salinity or with a pH different from the formation pH or waters containing organic acids such as oxalate or citrate or other complexing agents would aid in the dissolution and release from minerals such as feldspars or clays key nutrients such as phosphorous, nitrogen, potassium, cobalt or nickel. Alternatively phosphorus could be added as phosphate, polyphosphate or phosphorus pentoxide, nitrogen as ammonium ion or urea and potassium, cobalt or nickel as water soluble salts.

Monitoring the Process

During the injection process for stimulating microbial transformation of petroleums to methane and inhibiting microbial degradation of methane, both the formation conditions and the microbial dynamics (ecology) are preferably monitored. This monitoring can be performed in any suitable manner. Normally fluid (for example, oil, gas, and water) samples will be obtained from the formation through one or more wells in communication with the formation. The samples are analyzed to determine the concentration and type of microorganisms in the fluid as well as the concentration of modifiers and microbial products in the fluid. Other geochemical analyses may also be performed to assess the effectiveness of the stimulants on the formation environment and to confirm the chemical compatibility of the desired component to be injected and the subsurface fluids and solids. If based on this geochemical monitoring the modifier effect in the formation is outside the desired range, the concentration of modifier in the waterflood may be adjusted to bring the modifier concentrations back to within an acceptable range.

Production

Recovery of methane produced by the microbial activity can be by any suitable gas production technology, including infrastructure already in place in the field. The described process is not in any way restricted to secondary or tertiary oil recovery. The process can be used simultaneously with injection of water in secondary oil recovery, at the end of secondary recovery, or at the start of production of an oil field if and when injection of water is found feasible. After introduction of the stimulant package into the formation, the formation may be shut in for a sufficient period of time to allow the microorganisms to produce methane or production may be maintained throughout. The methane may accumulate in a gas zone or gas cap, a free-gas phase overlying an oil zone or as an enhanced methane concentration within the original oil phase. This gas may be withdrawn through a conventional gas production well that communicates with the gas zone or gas cap. In other formations, the gas may be produced as a product entrained in produced oil and water. In still other formations, the gas may be produced through different zones of wells previously used in production of liquid petroleums from the formation. To enhance microbial gas exsolution (release) from unrecoverable oil and subsequent gas production, it may be beneficial to drop the overall formation pressure by water well production or through natural pressure depletion as the petroleum is produced form the reservoir. This invention is not limited by the technology used to recover the methane or any associated oil, gas or condensate.

Biodegrading reservoirs allow novel forms of gas recovery. Layered reservoir bioreactors are discussed above.

While microorganisms can be injected into a reservoir formation microorganisms naturally present in the formation are preferred because it is known that they are capable of surviving and thriving in the formation environment. Indeed the inventors consider that the fields most favourable for petroleum recovery as methane are fields that are currently actively biodegrading. However, this invention is not limited to use of indigenous microorganisms. Exogenous microorganisms suitable for growing in the subterranean formation may be introduced into the formation by known injection techniques before, during, or after practicing the process of this invention.

The following field example illustrates a specific actual embodiment of the invention.

Figure 4:
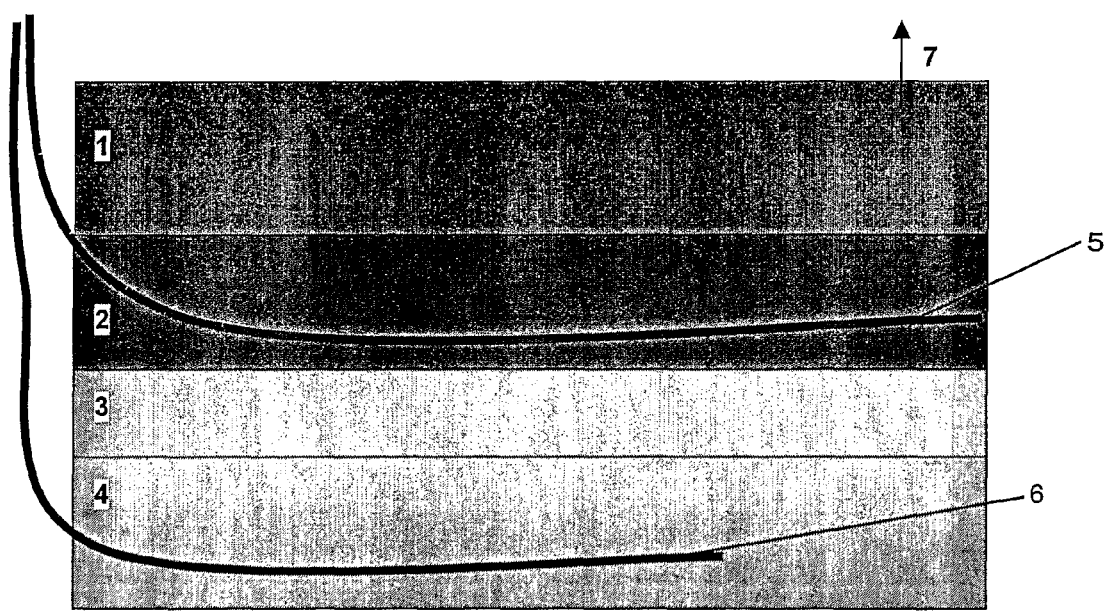
FIG. 4 shows a diagrammatic representation of an example of the invention.

For this hypothetical example, reference is made to FIG. 4 which illustrates a horizontal production or injection well 5 in a field with a mobile producible oil leg 2 and a residual oil zone 3 below it. A water leg 4 lies below the petroleum column. The oil leg 2 is overlain by a producible gas cap 1. The reservoir shows indications of active indigenous microorganisms (e.g. isotopically light carbon in methane, isotopically heavy carbon in carbon dioxide, compositional gradients in the oil or water column, detection of specific microorganisms). A horizontal injector well 6 underlies the petroleum accumulation. Oil production initially occurs from the upper production well 5 allowing water to migrate up through the residual oil zone 3 below the oil column 2. To facilitate methane production in the oil leg 2 or residual oil zone 3, by acceleration of the indigenous microorganisms, water containing one or more stimulants or adverse process suppressants may be periodically injected through the upper well 5 or injected through the lower injection well 6 into the water leg 4 or the residual oil zone 3.

As the subsurface microbes increase the conversion of oil in the pores to methane, the methane concentration (not shown) increases in the fluid phases (water and oil). Eventually the methane concentration may exceed the saturation level in the fluids and form bubbles of methane. The generated methane can migrate to the top of the formation to add to the existing gas cap 1 which is under production 7 or flow as dissolved gas in oil produced at an oil production well 5. The methane can for example be dissolved in oil in the mobile oil zone or dissolved in produced water. The methane can also flow as a separate gas phase along with produced oil and water. The methane is recovered at a production well along with produced oil and water. As oil and gas is produced the waters containing any injected stimulants or suppressants rises through the residual oil zone facilitating further accelerated conversion of oil to methane. Injection of fluid organic wastes such as sewage into the injector well below the petroleum column, or into the residual oil zone, would introduce microorganisms, nutrients and reactive organic matter which would produce abundant gas (methane and carbon dioxide), increase formation pressure improving oil recovery and produce gas bubbles which would aid in movement of waters up through the oil zones transporting nutrients and help transport methane through to the gas cap or oil leg where it can be produced in conventional production wells. Gas dissolving in the oil would decrease its viscosity and this together with any increase in pressure would facilitate oil recovery in addition to any methane production.

References

Aitken, C. M, Jones, D. M. & Larter, S. R. 2002, Isolation and identification of biomarkers indicative of anaerobic biodegradation in petroleum reservoirs., Abstracts of the 2002 William Smith Meeting, Geological Society of London, October, 2002. Full article in final review in Nature.

Anderson, R T & Lovley, D R. 2000. Hexadecane decay by methanogenesis, Nature, 404, 722-723.

Annweiler, E., Michaelis, W. and Meckenstock, R. U. Identical Ring Cleavage Products during Anaerobic Degradation of Naphthalene, 2-Methylnaphthalene, and Tetralin Indicate a New Metabolic Pathway. Applied and Environmental Microbiology, 68, 852-858 (2002).

Beller, H. R. (2002). Analysis of Benzylsuccinates in Groundwater by Liquid Chromatography/Tandem Mass Spectrometry and Its Use for Monitoring In Situ BTEX Biodegradation," Environmental Science and Technology 36, 2724-2728.

Bernard, F. P. and Connan, J., Indigenous microorganisms in connate waters of many oilfields: A new tool in exploration and production techniques. 67th Annual technical conference and exhibition of the Society of Petroleum Engineers, Vol. SPE 24811, Washington, D.C., 1992, pp. 467-476.

Bennett, P. C, Rogers, J R & Choi, W J, 2001. Silicates, silicate weathering, and microbial ecology., Geomicrobiol. J., 18, 3-19.

Boreham, C. J. Hope, J. M. & Hartung-Kagi, B. 2001. Understanding source, distribution and preservation of Australian natural gas: A geochemical perspective. APPEA Journal 41, 523-547.

Connan, J. 1984. in Advances in Petroleum Geochemistry, Vol. 1 (eds Brooks, J. & Welte, D. H.) 299-335. (Academic Press, London.)).

Dessort, D., Poirier, Y., Sermondadez, G. & Levache, D. 2003. Methane generation during biodegradation of crude oil. Abstracts of the 21st IMOG. Krakow, Poland, September 2003.

Ehrenberg S N, Jakobsen K G, Plagioclase dissolution related to biodegradation of oil in Brent Group sandstones (Middle Jurassic) of Gullfaks Field, northern North Sea. SEDIMENTOLOGY 48 (4): 703-721 AUG 2001

Gray, N. D. & Head, I. M. (2001). Linking genetic identity and function in communities of uncultured bacteria. Environmental Microbiology 3, 481-492

Hallam, S. J., Girguis, P. R., Preston, C. M., Richardson, P. M. and DeLong, E. F. (2003). Identification of methyl coenzyme M reductase a (mcrA) genes associated with methane-oxidizing archaea. Applied and Environmental Microbiology, 69, 5483-5491.

Head, I. M., Saunders, J. R. & Pickup, R. W. (1998). Microbial evolution, diversity and ecology: a decade of ribosomal RNA analysis of uncultured microorganisms. Microbial Ecology 35, 1-21

Head, I. M. (1999). Recovery and analysis of ribosomal RNA sequences from the environment. p. 139-174. In: Environmental Monitoring of Bacteria. edited by C. Edwards. Methods in Biotechnology Volume 12. Humana Press, Totowa, N.J.

Horstad, I. and Larter, S. R., Petroleum migration, alteration, and remigration within Troll field, Norwegian North Sea, Aapg Bulletin-American Association of Petroleum Geologists, 81 (1997) 222-248.

Head, I., Jones, D. M. & Larter, S. R. 2003. Biological activity in the deep subsurface and the origin of heavy oil. Nature, 426, 344-352.

James, A. T. & Burns, B. J. (1984) Microbial alteration of subsurface natural gas accumulations. AAPG Bulletin 68, 957-960.

Krüiger, M., Meyerdierks, A., Glöckner, F. O., Amann, R., Widdell, F., Kube, M., Reinhardt, R., Kahnt, J., Böcher, R., Thauer, R. K & Shima, S. 2003. A conspicuous nickel protein in microbial mats that oxidize methane anaerobically. Nature 426, 878-881

Larter, S., Hockey, A., Aplin, A., Telnaes, N., Wilhelms, A., Horstad, I., Di Primio, R. and O., S., When biodegradation preserves petroleum! Petroleum geochemistry of N. Sea Oil Rimmed Gas Accumulations (ORGA's). Proceedings AAPG Hedberg Research Conference on "Natural Gas Formation and Occurrence", Durango, Colo., 1999, pp. 3.

Larter, S. R., Wilhelms, A., Head, I., Koopmans, M, Aplin, A., Di Primio, R, Zwach, C., Erdmann, M. and Telnaes, N. (2003) The controls on the composition of biodegraded oils in the deep subsurface: (Part 1) Biodegradation rates in petroleum reservoirs, Organic Geochemistry, V34, 601-613(2003)

Lueders, T. and Friedrich, M. W. (2003). Evaluation of PCR amplification bias by terminal restriction fragment length polymorphism analysis of small-subunit rRNA and mcrA genes by using defined template mixtures of methanogenic pure cultures and soil DNA extracts. Applied and Environmental Microbiology, 69, 320-326.

Magot, M., Ollivier, B. & Patel, B.K.C. 2000, Microbiology of petroleum reservoirs, Antonie Van Leeuwenhoek International Journal of General and Molecular Microbiology, 77, 103-116.

Manning, D. A. C. and Hutcheon, I. E. Distribution and mineralogical controls on ammonium in deep groundwaters. Applied geochemistry, in press.

Masterson, W. D., et al. 2001. Evidence for biodegradation and evaporative fractionation in West Sak, Kuparuk and Prudhoe Bay field areas, North Slope, Ak., Org. Geochem. 32, 411-441.

Mueller, R. F. & Nielsen, P. H. 1996. Characterization of thermophilic consortia from two souring oil reservoirs, Applied and Environmental Microbiology, 62, 3083-3087.

Nazina, T. N., Ivanova, A. E., Borzenkov, I. A., Belyaev, S. S. & Ivanov, M. V. 1995. Occurrence and geochemical activity of microorganisms in high-temperature, water-flooded oil fields of Kazakhstan and Western Siberia, Geomicrobiology Journal, 13, 181-192.

Nazina, T. N., Ivanova, A. E., Golubeva, O. V., Ibatullin, R. R., Belyaev, S. S. & Ivanov, M. V., Occurrence of Sulfate-Reducing and Iron-Reducing Bacteria in Stratal Waters of the Romashkinskoe Oil-Field, Microbiology. 1995, 64, 203-208.

Ng, T. K., Weimer, P. J. & Gawel, L. J. 1989. Possible Nonanthropogenic Origin of 2 Methanogenic Isolates From Oil-Producing Wells in the San-Miguelito Field, Ventura County, Calif., Geomicrobiology Journal, 7, 185-192.

Nilsen, R. K. & Torsvik, T. 1996. Methanococcus thermolithotrophicus Isolated from north sea oil field reservoir water. Appl. Environ. Microbiol. 62, 1793-1798.

Orphan, V. J., Taylor, L. T., Hafenbradl, D. & Delong, E. F. 2000. Culture-dependent and culture-independent characterization of microbial assemblages associated with high-temperature petroleum reservoirs, Applied and Environmental Microbiology, 66, 700-711.

Obraztsova, A. Y., Shipin, O. V., Bezrukova, L. V. and Belyaev, S. S., Properties of the Coccoid Methylotrophic Methanogen, Methanococcoides-Euhalobius Sp-Nov, Microbiology, 56 (1987) 523-527.

Pallasser, R. J. 2000. recognising biodegradation in gas/oil accumulations through the dell3C composition of gas components., Org. Geochem., 31, 12, 1363-1373.

Rabus, R., Wilkes, H., Behrends, A., Armstruff, A., Fischer, T., Pierik, A. J. and Widdel, F. Anaerobic Initial Reaction of n-Alkanes in a Denitrifying Bacterium: Evidence for (1-Methylpentyl) succinate as Initial Product and for Involvement of an Organic Radical in n-Hexane Metabolism. Journal of Bacteriology, 183, 1707-1715 (2001).

Rogers J R, Bennett PC Mineral stimulation of subsurface microorganisms: release of limiting nutrients from silicates, CHEMICAL GEOLOGY, 203 (1-2): 91-108 Jan. 15 2004

Röling, W. F. M., & Head I. M. (2004). Prokaryotic systematics: PCR and sequence analysis of amplified 16 S rRNA genes. Advanced Methods in Molecular Microbial Ecology, Biosci Publishers.

Röling W. F. M., Head, I. M., & Larter, S. R. 2003. The microbiology of hydrocarbon degradation in subsurface petroleum reservoirs: perspectives and prospects, Research in Microbiology, 154, 321-328.

Rozanova, E. P., Savvichev, A. S., Karavaiko, S. G. & Miller, Y. M. 1995. Microbial Processes in the Savuiskoe Oil-Field in the Ob Region, Microbiology, 64, 85-90.

Scott, A. R., Kaiser, W. R. & Ayers, W. B. J. 1994. Thermogenic and secondary biogenic gases, San-Juan Basin, Colo. and New Mexico—Implications for coalbed gas producibility, Bulletin of the American Association of Petroleum Geologists, 78,1186-1209.

Stahl, D. A., (1997) Molecular Approaches for the measurement of density, diversity, and phylogeny. In: Manual of Environmental Microbiology (editors C. J. Hurst; G. R. Knudsen, M. J. McInerney, L. D. Stetzenbach, M. V. Walker), ASM press, Washington D.C., 1997, pp. 102-114.

Sweeney, R. E. & Taylor, P., 1999. Biogenic methane derived from biodegradation of petroleum under environmental conditions and in oil & gas reservoirs. In: Schoell, M., and Claypool, G. E., (Eds.), Proceedings of the AAPG Hedberg Research Conference, 6-10 Jun., 1999.

Truper, H. G. and Schleifer, K-H. (1992). Prokaryote Characterization and Identification. In: The Prokaryotes, Second Edition, (eds., A. Balows, H. G. Truper, M. Dworkin, W. Harder, K-H. Schleifer) 1992 Vol 1, pp. 126-148.

Wenger, L. M., Davis, C. L. & Isaksen, G. H. 2001. Multiple controls on petroleum biodegradation and impact in oil quality., SPE 71450, Society of Petroleum Engineers, 2001.

Widdel, F. & Rabus, R. 2001. Anaerobic biodegradation of saturated and aromatic hydrocarbons, Current Opinion in Biotechnology, 12, 259-276.

Wilhelms, A., Larter, S. R., Head, I., Farrimond, P., di-Primio R. & Zwach, C. 2001. Biodegradation of oil in uplifted basins prevented by deep-burial sterilisation., Nature 411, 1034-1037.

Wilkes, H., Rabus, R., Fischer, Th., Armstroff, A., Behrends, A. & Widdel, F. 2002. Anaerobic degradation of n-hexane in a denitrifying bacterium: Further degradation of the initial intermediate (1-methylpentyl) succinate via C-skeleton rearrangement. Archives of Microbiology, 177 (3): 235-243

Zengler, K., Richnow, H. H., Rossella-Mora, R., Michaelis, W. & Widdel, F. 1999. Methane formation from long-chain alkanes by anaerobic microorganisms. Nature 401, 266-269.

Annex 1
ATS10C SEQ ID: 1
GCTCATTAACATGTGGACAATCTACCCTTGGGTAGGGGATAACCTTGGGA
AACTGAGGATAAAACCCTATAGGCATAGAATGCTGGAATGCTTCTATGTT
AAAAGGCAACGCCCAAGGATGAGTCTGCAACCTATTAGGCTGTAGCAGGT
GTAATGCACTTGTTAACCTATGATGGGTACGGGCCATGAAAGTGGTTGCC
CGGAGATGGACTCTGAGACATGAGTCCAGGCCCTACGGGGCGCAGCAGGC
GCGAAAACTTCGCAATGTGCGCAAGCACGACGGGGGAATCCTAAGTGCCT
ATGCTTTGCATAGGCTGTTCTCCTGTCTAAAAAATAGGGGAAGTAAGGGC
TGGGTAAGACGGGTGCCAGCCGCCGCGGTAATACCCGCAGCCCAAGTGGT
GATCGTTATTATTGGGTCTAAAACGTCCGTAGCTGGTTTGGTAAATTCCT
GGGTAAATCGAGCTGCCTAACAGTTCGAATTCTGGGGAGACTGCCAGACT
TGGGACCGGGAGGAGTCAGAAGTACTTTCGGGGTAGGGTAAAATCCTGC
AATCCTGAAAGGACTATCAGCGGCGAAGGCGTCTGACCAGAACGGATCCG
ACAGTAAGGGACGAAGCCCTGGGGCGCAAACGGGATTAGATACCCCGGTA
GTCCAGGGTGTAAACGCTGTAGGCTTGGTGCTGGGGGTTCTACGAGGACA
CACAGTGCCGGAGAGAAGTTGTTAAGCCTACTACCTGGGGAGTACGGTCG
CAAGACTGAAACTTAAAGGAATTGGCGGGGGAGCACCGCAACGGGTGGAG
CGTGCGGTTTAATTGGATTCAACGCCGGAAAACTCACCGGGAGCGACGGT
TACATGAAGGCCAGGCTA ATS29a SEQ ID: 2
CACGTGGACAATCTACCCTTCGGTGGGGGATAATCTTGGGAAACTGAGAA
TAATACCCCATAGGCCTAGGATGCTGGAATGCTTCTAAGCTGAAAGTTCC
GACGCCGAAGGATGAGTCTGCCGGCCTATCAGGTTGTAGCAAGTGTAATGC
ACTTGTTAGCCTACAACGGGTACGGGCCATGAGAGTGGTTGCCCGGAGAT
GGACTCTGAGACATGAGTCCAGGCCCTACGGGGCGCAGCAGGCGCGAAAA
CTTCGCAATGTGCGCAAGCACGACGAGGGAATCCTAAGTGCCTATGCTTT
GCATAGGCTGTTCTCCTGTCTAAAAACAGGGGGAGTAAGGGCTGGGTAA
GACGGGTGCCAGCCGCCGCGGTAATACCCGCAGCCCAAGTGGTGATCGTT
ATTATTGGGTTTAAAATGTCCGTAGCTGGTCTAGTAAATTCCTGGGTAAA
TCGAATTGCTTAACAATTCGAATTCCGGGTAGACTGCTAGACTTGGGACC
GGAAGAAGTCAGAAGTACTTCTGGGGTAGGGGTAAAATCCTGTAATCCTG
GAGGGACTATCAATGGCGAAATTTCGGAAGCAAATCTTCCTCATTTATCG
TTGCTTCCGCAACGCTAAGGCGTCTGACTAGAACGGATCCGACAGTAAGG
GACGAAGCCCTGGGGCGCAAACGGGATTAGATACCCGGTAGTCCAGGGT
GTAAACGCTGTAGGCTTGGTGTTGGGGGTCCTATGAGGACATCCAGTGCC
GGAGAGAAATTGTTAAGCCTACTACCTGGGGAGTACGGTCGCAGGACTGA
AACTTAAAGGAATTGGCGGGGGAGCACCGCAACGGGTGGAGCGTGCGGTT
TAATTGGATTCAACGCCGGAAACCTCACCGGGGGCGACGGTTATATGAAG ATS29C SEQ ID: 3
CATGTGGACAATCTACCCTTGGGTAGGGGATAACCTTGGGAAACTGAGGA
TAAAACCCTATAGGCATAGAATGCTGGAATGCTTCTATGTTAAAAGGCAA
CGCCCAAGGATGAGTCTGCAACCTATTAGGCTGTAGCAAGTGTAATGCAC
TTGTTAACCTATGATGGGTACGGGCCATGAAAGTGGTTGCCCGGAGGTGG
ACTCTGAGACATGAGTCCAGGCCCTACGGGCGCAGCAGGCGCGAAAACT
TCGCAATGTGCGCAAGCACGACGAGGGAATCCTAAGTGCCTATGCTTTGC
ATAGGCTGTTCTCCTGTCTAAAAAATAGGGGAAGTAAGGGCTGGGTAAGA
CGGGTGCCAGCCGCCGCGGTAATACCCGCAGCCCAAGTGGTGATCGTTAT
TATTGGGTCTAAAACGTCCGTAGCTGGTTTGGTAAATTCCTGGGTAAATC
GAGCTGCCTAACAGTTCGAATTCTGGGGAGACTGCCAGACTTGGGACCGG
GAGGAGTCAGAAGTACTTTCGGGGTAGGGGTAAAATCCTGTAATCCTGAA
AGGACTATCAGCGGCGAAGGCGTCTGACCAGAACGGATCCGACAGTAAGG
GACGAAGCCCTGGGGCGCAAACGGGATTAGATACCCCGGTAGTCCAGGGT
GTAAACGCTGTAGGCTTGGTGCTGGGGGTTCTACGAGGACACACAGTGCC
GGAGAGAAGTTGTTAAGCCTACTACCTGGGGAGTACGGTCGCAAGACTGA
AACCTAAAGGAATTGGCGGGGAGCACCGCAACGGGTGGAGCGTGCGGTT
TAATTGGATTCAACGCCGGAAAACTCACCGGGAGCGACGGTTACATGAAG ATS13B SEQ ID: 4
TCTGAGTGCCTCCTAAGGAGGCTGTTCAGATGTTTAAAAAGCATCTGGAG
GAAGGGCTGGGCAAGACCGGTGCCAGCCGCCGCGGTAACACCGGCAGCCC
AAGTGGTAGTCCTGCTTACTGGGTCTAAAGCGTCCGTAGCCGGCCGGGTA
AGTTCCTTGGGAAATTTGATCGCTTAACGATCAAGCTACCTGGGAATACT
ACTTGGCTTGGGACCGGGAGAGGTCAGAGGTACTTCAAGGGTACGGGTGA
AATCCGTTAATCCTTGGGGGACCACCAGTAGCGAAGGCGTCTGATCAGAC
CGGATCCGACGGTGAGGGACNAAGGCTAGGGGAGCGAAGCGGATTAGATA
CCCGCGTAGTCCTGGCTGTAAACGATGCGGGCTAGGTATTGGCATTACTG
CNAGTGATGCCAGTGCTGAAGGGAATCCGTTAAGCCCGCCATCTGGGGAA
TACGGTCGCAAGGCTGAAACTTAAAGGAATTGNCGGGGGA ATS17A SEQ ID: 5
CCTAAGTGCCTATGCTTTGCATAGGCTGTTCTCCTGTCTAAAAAACAGGG
GGAGTAAGGGCTGGGTAAGACGGGTGCCAGCCGCCGCGGTAATACCCGCA
GCCCAAGTGGTGATCATTATTATTGGGTTTAAAATGTCCGTAGCTGGTCT
AGTAAATTCCTGGGTAAATCGAATTGCTTAACAATTCGAATTCCGGGTAG
ACTGCTAGACTTGGGACCGGAAGAGGTCAGAAGTACTTCTGGGGTACGGG
TAAAATCCTGTAATCCTGGAGGGACTATCAGTGGCGAAATTTCGGAAGCA
AATCTTCCTCATTTATCGTTGCTTCCGCAACGCTAAGGCGTCTGACTAGA
ACGGATCCGACAGTAAGGGACGAAGCCCTGGGGCGCAAACGGGATTAGAT
ACCCCGGTAGTCCAGGGTGTAAACGCTGTAAGCTTGGTGTTGGGGTCCT
ATGANGACATCCAATGCCGGAGAAAAATTGTTAAGCCTACTACCTGGGGA
GTACNGTCCGCAAGACTGAAACTTAAAGGAATTGGCGGGGGA ATS21C SEQ ID: 6
CTTAATGCCTATGCTTTTGCATAGGCTGTTCCCCTGTCTAAAAAATAGGG
GAAGTAAGGGCTGGGTAAGACGGGTGCCANCCGCCGCGGTAATACCCGCA
GCCCAAGTGGTGATCGTTATTATTGGGTCTAAAACGTCCGTAGCTGGTCT
GGTAAATTCCTGGGTAAATCGAGCTGCCTAACAGTTCGAATTCTGAGGAG
ACTGCCAGACTTGGGACCGGGAGGAGTCAGAAGTACTTTCGGGGTAGGGG
TAAAATCCTGTAATCCTGAAAGCGATCAGCGGCGAANGCGTCTGACCA
GAACGGATCCGACAGTAAGGGACGAAGCCCTGGGGCGCAAACGGGATTAG
ATACCCCGGTAGTCCAGGGTGTAAACGCTGTANGCTTGGTGCTGGGAGTT
CTACNANGACACCCANTGCCGGANAGAAGTTGTTAAGCCTACTACCTGGG
GAGTACGGTCGCAAGACTGAAACTTAAAGGAATTGGCGGGGGA ATS23A SEQ ID: 7
CTGAAGTGCCTCCTAAGGAGGCTGTTCAGATGTTTAAAAAGCATCTGGAG
GAAGGGCTGGGCAAGACCGGTGCCAGCCGCCGCGGTAACACCGGCAGCCC
AAGTGGTAGTCATGCTTACTGGGTCTAAAGCGTCCGTAGCCGGCCGGGTA
AGTTCCTTGGGAAATTTGATCGCTTAACGATCAAGCTACCTGGGAATACT
ACTTGGCTTGGGACCGGGAGAGGTCAGAAGTACTTCAAGGGTAGGGGTGA
AATCCGTTAATCCTTGGGGGACCACCAGTAGCGAAGGCGTCTGATCAGAC
CGGATCCGACGGTGAGGGAACGAGGCTANGGGAGCNAAGCGGATTAGATA
CCCGCGTAGTCCTAGCTGTAAACGATGCGGGCTAGGTATTGGCATTACTG
CGAGTGATGCCAGTGCCGAAGGAAGCCGNTAAGCCCGCCATCTGGGGAA
TACGGTCGCAANGCTTAAACTTAAAGGAATTGGCGGGGGA

The invention claimed is:

1. A process for stimulating microbial methane production in a petroleum-bearing subterranean formation, in which a microbial consortium comprising at least one methanogenic microorganism and one or more methanotrophic microorganisms are present, comprising:
   (a) analyzing one or more components of the formation to determine characteristics of the formation environment;
   (b) detecting the presence of the microbial consortium, comprising at least one methanogenic microorganism, within the formation;
   (c) assessing whether the formation microorganisms are currently active;
   (d) determining that the microbial consortium comprises one or more methanotrophic microorganisms, and assessing whether said one or more methantrophic microorganisms are active;
   (e) characterizing one or more microorganisms of the consortium, at least one of the members of the consortium being a methanogenic microorganism, and comparing the members of the consortium with at least one known microorganism having one or more known physiological and ecological characteristics;
   (f) characterizing one or more methanotrophic microorganisms of the consortium, and comparing the members of the consortium with at least one known microorganism having one or more known physiological and ecological characteristics;
   (g) using information obtained from steps (a) through (e) for determining an ecological environment that promotes in situ microbial degradation of petroleum and promotes microbial generation of methane by at least one methanogenic microorganism of the consortium;
   (h) using information obtained from steps (a) and (f) for determining an ecological environment that demotes in situ microbial degradation of methane by at least one methanotrophic microorganism of the consortium; and
   (i) modifying the formation environment based on the determinations of steps (g) and (h) to stimulate microbial conversion of petroleums to methane while minimizing methane destruction by adverse processes.

2. A method according to claim 1, wherein the step of detecting the presence of anaerobic oil-degrading bacteria is part of step (b).

3. A method according to claim 1, which includes identifying products of indigenous microbial activity.

4. A method according to claim 3, wherein the products identified include anaerobic hydrocarbon degradation metabolites.

5. A method according to claim 1, which includes identifying archaeols.

6. A method according to claim 1, wherein the analysis in step (a) is focused on the oil-water transition zones in the formation.

7. A method according to claim 1, wherein geochemical proxies are used to assess whether the formation is actively degrading.

8. A method according to claim 1, wherein step (e), and step (f) are characterized using genetic characterization methods.

9. A method according to claim 8, wherein the genetic characterization methods include comparison of sequences of genetic fragments sampled from the microorganisms against sequences from known microorganisms.

10. A method according to claim1, wherein the step of modifying the formation environment includes introducing an additive selected from:
    (a) major nutrients;
    (b) vitamins;
    (c) trace elements;
    (d) buffers;
    (e) waters of: (i) different salinities;
        (ii) different pH values;
        (iii) containing complexing agents;
    (f) inhibitors for methane degradation activity.

11. A method according to claim 10, wherein the concentration of phosphorus in the formation environment is increased.

12. A method according to claim 10, wherein the concentration of ammonium ion in the formation environment is increased.

13. A method according to claim 10, wherein the concentration of potassium in the formation environment is increased.

14. A method according to claim 1, wherein the step of modifying the formation environment includes gas sparging or flushing.

15. A method according to claim 1, wherein the step of modifying the formation environment includes injection of reactive liquid organic matter into the formation.

* * * * *